(12) United States Patent
Gephart et al.

(10) Patent No.: US 9,486,248 B2
(45) Date of Patent: Nov. 8, 2016

(54) OCCIPITAL PLATE FOR SPINAL FUSION

(71) Applicant: Pioneer Surgical Technology, Inc., Marquette, MI (US)

(72) Inventors: Matthew P. Gephart, Marquette, MI (US); Phillip J. Berman, Jacksonville, FL (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 0 days.

(21) Appl. No.: 14/665,938

(22) Filed: Mar. 23, 2015

(65) Prior Publication Data

US 2015/0257794 A1   Sep. 17, 2015

Related U.S. Application Data

(63) Continuation of application No. 12/983,207, filed on Dec. 31, 2010, now Pat. No. 8,986,351.

(60) Provisional application No. 61/298,488, filed on Jan. 26, 2010.

(51) Int. Cl.
*A61B 17/80* (2006.01)
*A61B 17/70* (2006.01)

(52) U.S. Cl.
CPC ........... *A61B 17/7055* (2013.01); *A61B 17/70* (2013.01); *A61B 17/7002* (2013.01); *A61B 17/7059* (2013.01)

(58) Field of Classification Search
CPC .............. A61B 17/70; A61B 17/7002; A61B 17/7032; A61B 17/7034; A61B 17/7035; A61B 17/7037; A61B 17/704; A61B 17/7044; A61B 17/7055; A61B 17/7059; A61B 17/80; A61B 17/8004
USPC .................... 606/280–299, 70, 71, 903, 246, 606/250–253
See application file for complete search history.

(56) References Cited

U.S. PATENT DOCUMENTS

| | | | |
|---|---|---|---|
| 5,735,853 A * | 4/1998 | Olerud | 606/71 |
| 6,524,315 B1 | 2/2003 | Selvitelli et al. | |
| 6,902,565 B2 | 6/2005 | Berger et al. | |
| 7,141,051 B2 | 11/2006 | Janowski et al. | |
| 7,303,563 B2 | 12/2007 | Poyner et al. | |
| 2004/0153070 A1 | 8/2004 | Barker et al. | |
| 2006/0149252 A1 | 7/2006 | Markworth et al. | |
| 2007/0025711 A1 | 2/2007 | Marcus | |
| 2007/0233119 A1 | 10/2007 | Markworth | |
| 2008/0045955 A1 | 2/2008 | Berrevoets et al. | |
| 2008/0051783 A1 | 2/2008 | Null et al. | |
| 2008/0086124 A1 | 4/2008 | Forton et al. | |
| 2008/0125781 A1 * | 5/2008 | Hoffman et al. | 606/69 |
| 2009/0062915 A1 | 3/2009 | Kohm et al. | |
| 2010/0222779 A1 * | 9/2010 | Ziemek et al. | 606/71 |
| 2011/0106085 A1 | 5/2011 | Null et al. | |

* cited by examiner

*Primary Examiner* — Kevin T Truong
*Assistant Examiner* — Si Ming Ku
(74) *Attorney, Agent, or Firm* — Fitch, Even, Tabin & Flannery LLP

(57) ABSTRACT

Plate devices are provided for mounting to bone and receiving one or more spinal rods. The devices may include coupling members or rod receiving members coupled to the plate member and configured to have multiple degrees of adjustability in order to accommodate elongate connecting members of various orientations. The plate devices may also include quick locking features or locking devices that secure multiple points of articulation simultaneously.

18 Claims, 50 Drawing Sheets

OCCIPITAL PLATE FOR SPINAL FUSION

CROSS-REFERENCE TO RELATED APPLICATIONS

This application is a continuation of U.S. application Ser. No. 12/983,207, filed Dec. 31, 2010, which claims benefit of U.S. Provisional Application 61/298,488, filed Jan. 26, 2010, which is hereby incorporated herein by reference in its entirety.

FIELD OF THE INVENTION

The invention relates generally to devices for securing the ends of spinal rods or other elongate fixation members to the skull of a patient for spinal repair and/or fusion surgeries.

BACKGROUND OF THE INVENTION

Rigid or semi-rigid elongate members, such as spinal rods, may be mounted to the spinal column in order to stabilize or immobilize vertebrae of the spinal column for a variety of purposes. For instance, spinal rods are often secured to adjacent vertebral bodies via anchor members in order to promote fusion of the two vertebrae as a treatment for degenerative disc disease, spondylolisthesis, spinal stenosis, fractures of the vertebrae, and other conditions. Limiting or preventing motion of the vertebrae promotes the healing process. By removal of the disc positioned between the vertebrae and limiting motion between the vertebrae, the adjacent boney surfaces are allowed to grow into one another and fuse together. Fusion devices may also be placed between the two immobilized vertebrae in order to facilitate the process of fusion.

When stabilizing portions of the spinal column, and in particular the cervical region of the spine, it is sometimes necessary to immobilize the skull in addition to vertebrae. The same elongate rigid structures used to link and stabilize the vertebrae may therefore be secured to the skull in order to keep the skull in an appropriate spatial relationship with respect to the spinal column. However, since the anatomy and thickness of the skull and its surrounding tissues are very different than those of the vertebrae and their surrounding tissues, the elongate rigid structures must be anchored to the skull in a different manner than that used for the vertebrae.

For instance, in many spinal stabilization procedures elongate rods made of titanium or other materials are placed adjacent to the posterior side of the spine and anchored in place using screws connected to some type of coupling assembly. Examples of suitable coupling assemblies for posterior fixation systems are disclosed in U.S. Pat. No. 7,141,051; U.S. Published Application No. 2008/0045955; and U.S. Published Application No. 2007/0225711. The screws used to anchor these devices and other coupling assemblies are often relatively long, and are mounted to the pedicle area of the vertebrae with the shanks of the screws penetrating deep into the vertebral body. The yoke portion of the coupling assembly that is coupled to the screw and receives the spinal rod is nested between outwardly-extending boney processes so that the height of the yoke is not noticeable.

When spinal rods are mounted to the skull, however, long screws and large coupling assemblies cannot be mounted directly to the skull without undue risk of penetrating the brain encased therein. Many coupling assemblies also would prove extremely and unduly cumbersome if mounted directly to the skull, and may even protrude significantly from the back of the head. In addition, the occipital region, which juts out at the base of the skull, is the only reasonable site at which to mount an internal fixation system, requiring that spinal rods connected thereto be bent severely in order to be positioned along the occipital region and be connected to the occipital region in a manner similar to the connection to the vertebrae.

Previous systems for coupling spinal rods and other elongate stabilization devices to the skull vary. However, most systems utilize a plate mounted to the occipital region of the skull that attaches to a rod, cable, wire, plate, or screw mounted to a region of the spine. In most spinal rod systems, two spinal rods are positioned generally parallel to the surface of the plate and then secured thereto by a bracket or u-shaped receiving member. The plates are mounted to the skull with several small screws disposed along the full length and width of the plate. Since the base of the skull angles inward toward the spine, the plates mounted to the skull are not parallel to the posterior surfaces of the vertebrae, and the spinal rods must be bent significantly away from the vertebrae in order to reach the occipital region in an orientation that may be mounted to the plate. For instance, the bending of spinal rods in order for them to properly be received relative to an occipital plate is shown in the devices of FIGS. 1, 2, and 18 of U.S. Published Application No. 2004/0153070. In that device, spinal rods mounted along the vertebrae must be manipulated in order to fit precisely into receiver mechanisms aligned along the sides of a plate designed to be fixed to the occipital region of the skull. This bending of the rod can fatigue the rod material, and also makes it difficult to reposition the elements of the stabilization system.

Even attempts to provide occipital plate devices with adjustability in order to accommodate spinal rods of various orientations still generally require significant manipulation and bending of spinal rods before they can be secured to the plate structure. For instance, U.S. Pat. No. 6,902,565 discloses a plate designed to be mounted to the occipital region of the skull by a plurality of short expansion head screws. The plate receives a pair of rods that may be further mounted to one or more vertebrae. In many cases these rods are pre-bent so that the majority of the rods may be positioned parallel to the spine, with the ends bent transversely in order to be secured to the plate by a clamp plate or bracket. Some embodiments include plates that are bent in order to receive the rods that are parallel to the spine. However, in all cases the devices provided to clamp the rods in place on the plate are designed to accept the rod in only one position, so that any variation in angle or spacing of the rods caused by the patient's anatomy requires bending of the spinal rods in order to properly secure them to the plate.

U.S. Published Application No. 2008/0051783 discloses a plate device having a pair of u-shaped rod receiving members that protrude from lateral wings of the plate. The wings may be shifted laterally and medially, and the rod receiving members may rotate to adjust the direction in which a connecting member (such as a spinal rod) is received. Therefore, the device does allow some adjustability in order to receive the spinal rods. However, the spinal rods must be positioned so that they are generally parallel to the plate surface in order to fit into the rod receiving members. Therefore, the ends of the rod must be bent away from the axis of the spine and into the u-shaped channels of the receiving members.

U.S. Pat. No. 6,524,315 discloses a plate secured to the bone by a plurality of screws. The plate is fitted with slotted bolts designed for receiving a rod or cable. The base of the slotted bolt is recessed in the plate at its base. A support platform may be fitted over the bolt to help hold the rod or cable. A nut fastens over the threaded end of the slotted bolt to trap the rod or cable within the bolt, securing it to the plate. While the bolt may be rotated to adjust the direction of the rod or cable, this adjustment affects only one plane, and does not allow for adjustment of the angle of the rod or cable with respect to the surface of the plate.

U.S. Published Application 2007/0233119 discloses a plate device with polyaxial connector head assemblies including a connector body that receives a spinal rod and a connector head pivotably connected to the connector body and configured to be secured to the plate so that the connector assemblies provide limited polyaxial movement of the spinal rods with respect to the plate. However, the device does not allow multiple types of movement to provide a highly articulated device. Furthermore, the coupling heads are relatively bulky and still hold the spinal rods relatively parallel to the plate surface.

Therefore, improved devices for securing spinal rods to the occipital region of the skull are desirable.

SUMMARY OF THE INVENTION

Fixation devices are provided herein for mounting to bone and receiving one or more spinal rods. Typically, these systems include a plate member that is curved to generally mate with the surface of the skull or another boney region. The devices also include coupling members or rod receiving members coupled to the plate member and configured to have multiple degrees of adjustability in order to accommodate elongate connecting members of various orientations. Although the devices may be configured to secure a number of elongate connecting members, such as rods, cables, wires, and the like, spinal rods will be primarily discussed herein. It will be understood, however, that this description is not intended to be limiting, and that the invention is intended to be adapted for use with a variety of connecting members of different shapes, sizes, and configurations.

In one aspect of the invention, a spinal rod mounting device may be provided that includes a plate member having a plurality of openings for receiving anchor devices and a pair of rod receiving members slidably or pivotably adjustable with respect to the plate member. In one preferred form, the rod receiving members are configured to receive a spinal rod such that the spinal rod can extend therefrom in a plurality of different directions relative to the plate member so that the rod receiving members provide adjustability for the rods extending therefrom. Once the desired direction is selected, the rod can be locked in place in the receiving member so as to fix the selected direction of the rod extending therefrom. The rod receiving devices also may be positioned so that they can be secured to a portion of an elongate member that is orthogonal to the surface of the plate member.

In another preferred aspect, the rod receiving members are slidably coupled to the plate member. In another preferred form, the rod coupling devices are mounted to the plate member in a manner that allows the rod receiving devices to pivot with respect to the plate member. In a more preferred aspect the rod receiving devices are both slidable and pivotable with respect to the plate member to provide multiple degrees of adjustability.

In another aspect, which may be optionally combined with other aspects of the invention, the rods and/or rod receiving devices may be configured to be received by the rod receiving members in a plurality of orientations with respect to the rod receiving members. For instance, the rods may be provided with enlarged, curvate heads sized to be received in a pocket or cavity of the rod receiving device such that the curvate head may be pivoted to a plurality of positions within the interior of the cavity. Preferably, the cavity of the rod receiving devices are provided with curvate interior surfaces contoured to generally mate with the curvate exterior of the rod heads. Preferably, the rod heads and cavities are both partially spherical in order to provide ball-and-socket connections between the spinal rods and rod receiving members. This allows the axes of the elongate spinal rods to be positioned to extend in a variety of different directions from the rod receiving device without requiring bending of the spinal rods for this purpose. The direction of the spinal rod may be locked with respect to the rod receiving device by a locking member, such as a set screw, non-threaded camming member, or other device that forces the spinal rod against the interior of the rod receiving member to create frictional forces that inhibit movement between the rod and the rod receiving device. Combined with sliding and pivoting adjustability of the rod receiving members, this ball-and-socket connection between the spinal rods and rod receiving device provides a highly adjustable system that can receive a pair of spinal rods having various orientations and hold the pair of spinal rods in a fixed relationship with respect to a plate member attached to a patient's skull.

In another aspect, a plate device may be provided with a simple to operate rapid locking mechanism to quickly secure the spinal rods in place without separate adjustment of multiple parts. This allows the position of one or more spinal rods to be fixed with respect to the plate device without adjusting multiple and/or complex parts.

The plate may be relatively thin and contoured to rest against the lower rear surface of a patient's skull. The rod receiving members may each have an arm portion to serve as a connection point to the corresponding plate arms, and the rod receiving members may be secured to the arms of the plate by a bolt or other pivot member about which the rod receiving device is able to pivot. Each bolt is preferably disposed within a slot in an arm of the plate so that the rod receiving member is able to slide relative to the plate member. In one aspect of the invention, the arms and corresponding slots of the plate member are disposed so as to extend away from the center axis of the plate member so that the rod receiving devices may slide along the slots of the plate arms in order to adjust the distance between the rod receiving devices and the center of the plate member. Pivoting of the rod receiving devices allows the rod receiving devices to be positioned at a plurality of positions along an arc centered around the bolt or other pivot member connecting the rod receiving device to the plate arm. Combining the pivoting and sliding movement of the arms and/or rod receiving devices allows for the rod receiving devices to extend in a variety of different directions and spatial relationships with respect to the plate member and one another. Preferably, the bolt or other connector may be tightened to lock the arm portion against sliding and pivoting, which in turn locks the position of the rod receiving member. Alternatively, a separate locking mechanism may be provided in order to prevent movement of the rod receiving member.

The rod receiving device may include a pocket or cavity for receiving the end of a spinal rod, or may have a channel that allows the spinal rod to pass therethrough. A locking member may be configured to fix the position of the rod with respect to the rod receiving device. For instance, the locking member may be a set screw that is threaded into the rod receiving device and clamps the spinal rod end therein, fixing the position of the rod through friction by pressing the rod against the interior of the rod receiving device.

In another aspect of the invention, a plate member may include a track portion having guide tracks in which a pair of yoke members are slidably disposed. The sliding of the yoke members along the guide tracks allows the distance between the yoke members to be adjusted so that the yoke members may capture spinal rods adjusted to various distances from one another. In addition, the yokes may be rotatably and/or pivotably coupled to the guide tracks in a polyaxial manner that allows for rotation and/or pivoting in one or more planes in order to easily capture spinal rods so that they extend in a variety of different directions relative to the plate member, and specifically the track portion thereof. For instance, the yoke may be provided with a swiveling neck portion that is slidably received in the track member and allows the yoke member to swivel in one or more directions with respect to the track member.

In one preferred form, the yoke member may rotate about an axis of the neck portion so that a rod receiving channel or opening in the yoke may be positioned to face in various different directions with respect to the direction in which the yoke slides along the track member. In another preferred aspect of the invention, the neck member forms a ball-and-socket connection with the yoke member in order to allow pivoting of the yoke member in at least two planes in addition to rotation about an axis of the neck portion. Locking members may be provided in order to secure the spinal rods to the yoke members and to fix the position of the yoke members with respect to the track member and plate member. In one aspect of the invention, a single locking member associated with each yoke member fixes the position of a spinal rod with respect to the yoke member and fixes the pivoted and rotated position of the yoke member with respect to the neck portion and/or track member. In another aspect, a single locking member secures the position of two yoke members along the track member, such as by adjusting a clamp member that spans the length of the track member to exert frictional forces that prevent the yoke members from sliding relative to the track member. Alternatively, separate clamping members may be provided to prevent the sliding of each of the yoke members.

In another aspect of the invention, the rod receiving members may be coupled to the plate member by telescoping members that allow the distance of the rod receiving members from the plate member to be adjusted. This may include, for instance, a sleeve portion having an axial bore coupled to the plate member and a post member coupled to the rod receiving member, with the post member slidably received in the axial bore of the sleeve portion. Alternatively, the sleeve portion may be coupled to the rod receiving member and the post coupled to the plate member. The sleeve and post members also may be pivotably coupled to the plate member and/or rod receiving member in order to provide further adjustability to the positioning and orientation of the rod receiving members.

In another form, one or more rod receiving members may be coupled to a plate member by two or more ball-and-socket connections. A housing may be provided to connect one ball-and-socket connection to the next. In one preferred form, a single locking member is associated with each housing and is configured to lock the position of both ball-and-socket connections with respect to the housing. The ball-and-socket connections also may be pivotably and/or slidably connected to the plate member and/or the rod receiving member to provide further adjustability to the device.

The anchors used to secure the plate to the patient's skull may be expandable in order to increase their holding strength. For instance, the shank of the screw may be hollow and have one or more slits therein running parallel to the axis of the shank so that insertion of a pin or other member into the hollow shank causes the exterior of the shank to splay, expanding the width of the shank and applying additional lateral force against the bone adjacent to the shank exterior. This lateral force increases the load that may be placed on the screw in an axial direction before the screw is stripped out of the bone.

DETAILED DESCRIPTION

Figure 1:
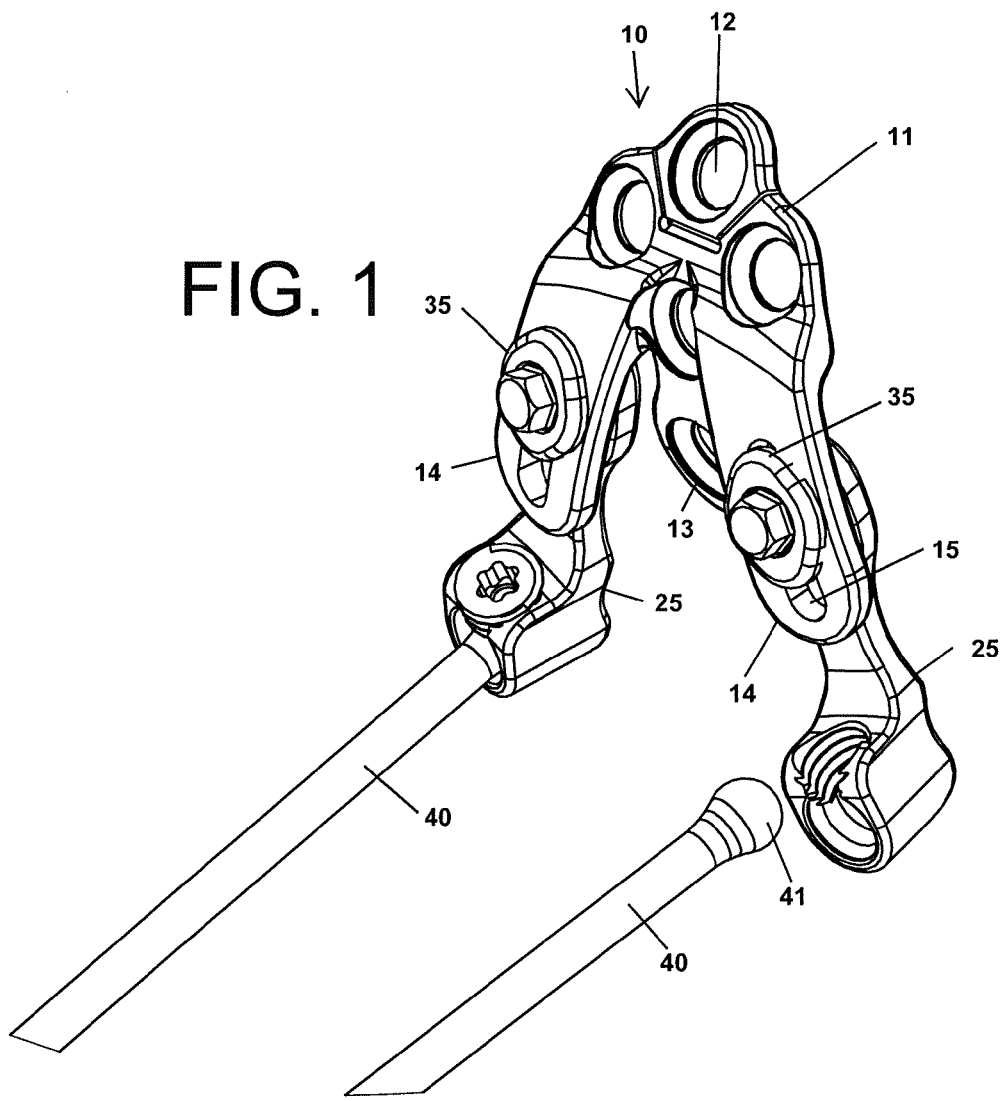
FIG. 1 is a first occipital plate device having sliding and pivoting rod receiving members that receive a pair of spinal rods in a polyaxial arrangement.

The novel plate devices disclosed herein are better designed to receive and hold spinal rod members than prior art plate devices configured for mounting to the occipital region of the skull. For instance, to illustrate the contrast between the presently disclosed occipital plate devices and the prior art, a prior art device that requires spinal rods to be bent substantially to be received by the plate device attached to the skull is shown in FIG. 1. A clamping device 3 on each side of the plate 2 secures an end of a spinal rod 5 parallel to the plate surface. The clamping device may include a threaded set screw that clamps against the spinal rod, a bracket that is secured against the rod, or the like. A series of pedicle screws 7 secure the rods 5 to the vertebrae. Since the plate 2 and clamp devices 3 are mounted transverse to the axis of the spine, the spinal rods 5 must be bent outward away from the spine in order to connect to the plate 2.

The plate devices provided herein have improved adjustability and/or are more easily locked to fix the spinal rods in place.

One embodiment of an occipital plate member with adjustable rod receiving heads is shown in FIGS. 1 through 8. The illustrated device includes a relatively flat plate member 10 configured to be secured to the patient's skull. Note that, although the plate member is relatively flat, it need not be planar, and preferably has a slight curvature to match the surface of the occipital region of the skull. The plate may also be provided with grooves or notches 19 at particular points along its surface in order to enhance the bendability of the plate at those points in order to better match the curvature of the skull.

The plate member 10 includes a plurality of apertures 12 for receiving anchor members that secure the plate member 10 to the skull. The apertures 12 may have tapered surfaces in order to center the anchor members disposed therein. For instance, the rim 17 surrounding each aperture may be curved or beveled in order to form a spherical or conical seating surface for the head of an anchor member. The plate body includes a lower lobe portion 13 for mounting to the surface of the skull and lateral arm portions 4 that diverge from the surface of the skull when the plate 10 is mounted. The arms 14 serve as connection points for rod receiving members.

Figure 2:
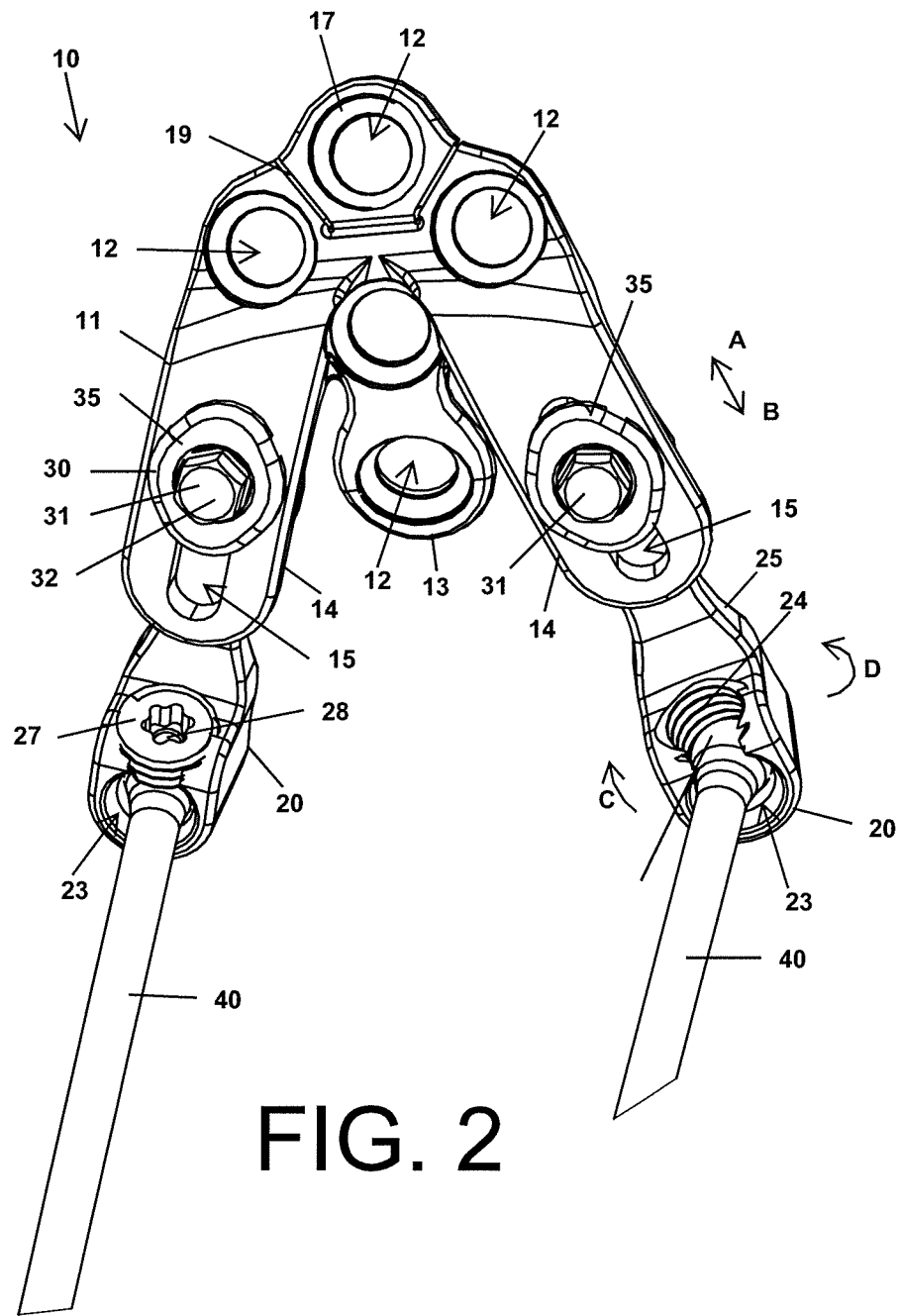
FIG. 2 is a perspective view of the occipital plate device shown in FIG. 1.
Figure 3:
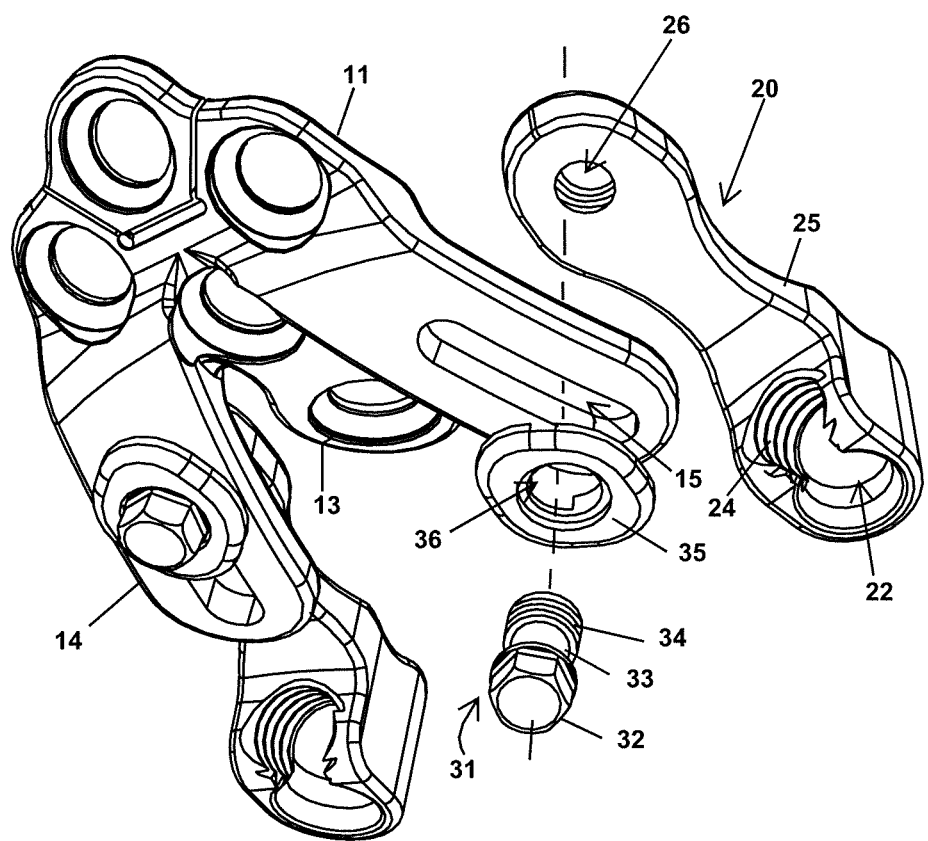
FIG. 3 is a perspective partially exploded view of the plate device of FIGS. 1 and 2 from the front.
Figure 4:
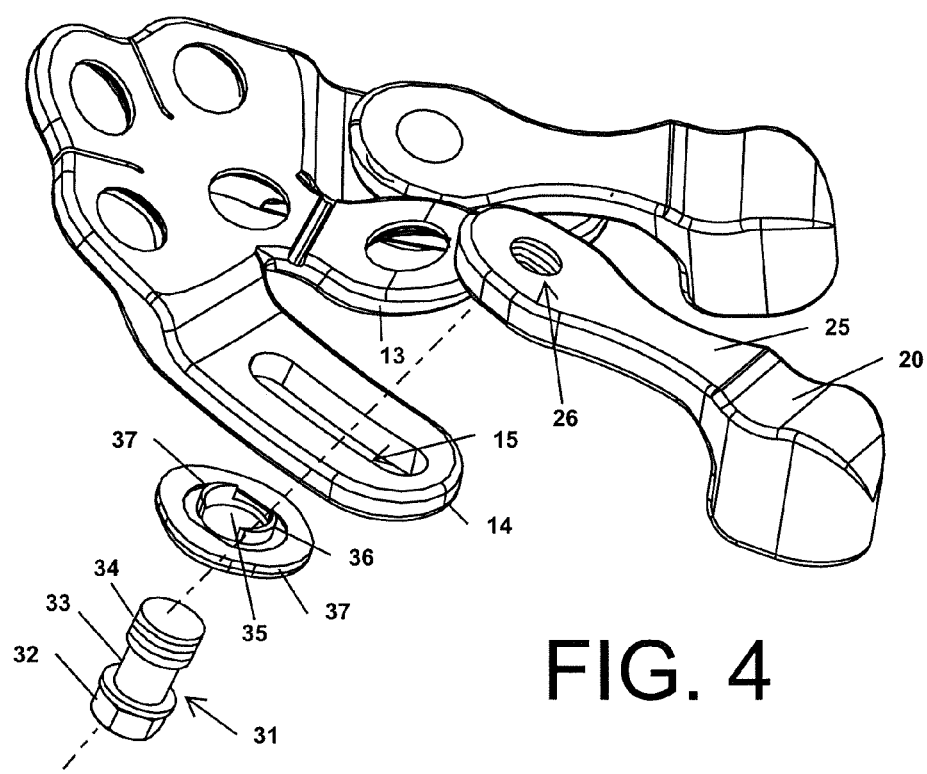
FIG. 4 is a perspective partially exploded view of the plate device of FIG. 1 from the rear.

In the device of FIGS. 1-8, rod receiving heads 20 are coupled to the plate member 10 by a sliding pivot connector 30. As shown in FIGS. 3 and 4, the sliding pivot connector includes a bolt 31 and a sliding member or washer 35 with an opening 36 in which the bolt 31 is received. The bolt 31 has an enlarged head 32 and a narrower shank portion 33 that is slidably disposed in the slot or guide track 15 of the plate's lateral arm 14 and threadably connected to the opening 26 in the arm 25 of a rod receiving device via a threaded shank portion 34.

The spinal rods 40 and rod receiving devices 20 shown in FIG. 2 are designed to interact in a polyaxial manner. The rods 40 each have a partially spherical or curvate head 41 that is enlarged with respect to the body of the rod 40. The rod head 41 may be formed integral with the rod 40, or may be a separate member that is secured to the rod 40 by a threaded connection, welding, or any other method. A cavity 22 (but seen in FIG. 3) in the rod receiving member 20 is configured to receive the enlarged head 41. The cavity may be semispherical or curved if desired in order to receive the rod head 41 to form a ball and socket connection, allowing the rod 40 to be pivoted to a number of different angles with respect to the rod receiving device 20 while still having the rod head 41 fully seated within the cavity 22 of the rod receiving device. A locking member is provided in order to prevent the rod head 41 form exiting the cavity 22. The locking member 27 may be a set screw or similar device, although the configuration of the locking member is not crucial as long as it is capable of engaging the rod receiving member 20 and securing the rod head 41 thereto. The locking member 27 shown includes an internal tool interface 28 to facilitate rotation of the locking member in order to advance the locking member along the threaded aperture of the receiving member.

In the illustrated embodiment, the locking member 40 is inserted into a threaded aperture 24 of the rod receiving device and into contact with the rod head 41 positioned within the rod receiving device. When the locking member 27 is fully threaded into the aperture 24, the leading end of the locking member presses against the rod head 41, forcing the rod head against the interior surface of the receiving device 20, applying frictional forces that prevent the rod 40 from further pivoting. This provides the device and the spinal rods connected thereto with structural rigidity in order to partially or fully immobilize the skull and spinal column. The cavity 22 of the receiving member 20 may be sized to mate closely with the exterior of the curvate spinal rod head 41 in order to increase the frictional forces that prevent pivoting of the rod 40.

The threaded aperture 24 for the locking member may, but need not, intersect with the opening 23 that receives the rod head 41, as long as the rod receiving device 20 still has the structural integrity to hold the rod head 41 in place once the locking member 27 is in a fully locked position.

The rod receiving device 20 may be positioned at various distances and angles with respect to the plate body 11 due to an articulated coupling between the receiving device 20 and the plate arm 14. Sliding of the connector 35 along the guide track 15 in the arm of the plate (back and forth along directions A and B) adjusts the distance of the receiving member 20 from the center of the plate. Since the guide tracks 15 of the two plate arms are disposed at oblique angles relative to the midline of the plate and one another, sliding of the bolt 31 therethrough may be used to simultaneously adjust the lateral distance between the two rod receiving members 20 and the overall length of the plate device. However, the receiving devices 20 may also pivot about their respective bolts 31. For instance, the rod receiving member 20 on the right side of the device in FIG. 2 may swing inward (medially) in direction C to return closer to the midline of the plate and the spine, and may swing outward (laterally) in direction D in order to increase the spacing of spinal rods received thereby. Through a combination of sliding and pivoting movement, the rod receiving members 20 may be adjusted to a multitude of positions to receive spinal rods of various spacings and orientations.

The sliding pivot connector 30 allows the receiving device 20 to be locked against both sliding and pivoting movement by manipulating a single locking member. The turning of the bolt 31 of the sliding pivot connector in a first direction clamps the rod receiving device arm 25 against the plate lateral arm 14, locking the position of the two components relative to one another. Rotation of the bolt 31 in an opposite direction releases the clamping force between the rod receiving device arm 25 and the plate lateral arm 14, allowing the rod receiving device 20 to pivot about the bolt 31. Therefore, a surgeon may swing the arm 25 of the rod receiving device 20 into position so that the cavity 22 of the device properly receives a spinal rod, whereupon the surgeon may tighten the bolt 31 in order to prevent further movement of the rod receiving device 20 with respect to the plate member 20.

The sliding member 35, in addition to being disposed between the head 32 of the bolt and the plate arm 14 and acting as a washer and to help secure the bolt 31, may also extend into the guide track 15 in order to better guide the sliding pivot connector. For instance, as shown in FIG. 4, the sliding member 35 may include projections 37 on the underside thereof that are fitted to be received in the guide track 15 of the plate arm 14.

FIGS. 3 and 4 illustrate that a lower lobe 13 of the plate body 11, which is positioned between the lateral arms 14 of the plate, curves upward relative to the arms 14. The lower lobe 13 is configured to follow the contours of the skull, maintaining contact with the bone while the arms 14 extend away from the skull at an angle. This configuration positions the rod receiving members 20 away from the skull to provide clearance for the receiving members to better receive the spinal rods connected to the spinal column.

Figure 5:
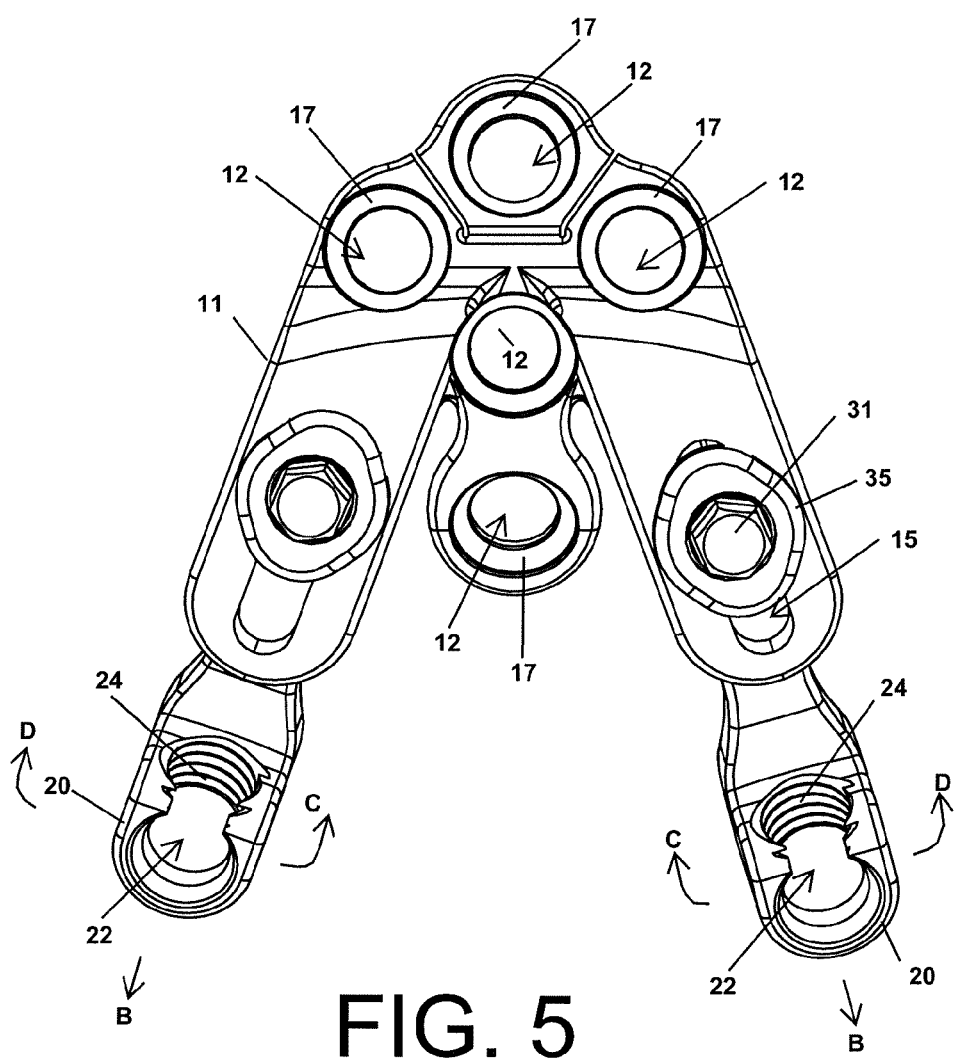
FIG. 5 is a plan view of the plate device of FIGS. 1-4.

The plate device of FIG. 1 is shown in plan view in FIG. 5. The sliding member 35 and connecting bolt 31 may slide along guide track 15 in order to extend the receiving devices outward in direction B. The rod receiving devices 20 are also capable of pivoting about the bolts 31 in order to swing laterally in direction D or medially in direction C. Each rod receiving device 20 may be separately adjusted in order to best receive a spinal rod. The spinal rods are not disposed in the receiving members in this figure, providing an unobstructed view of the spherical cavities 22 of the rod receiving members 20.

Figure 6:
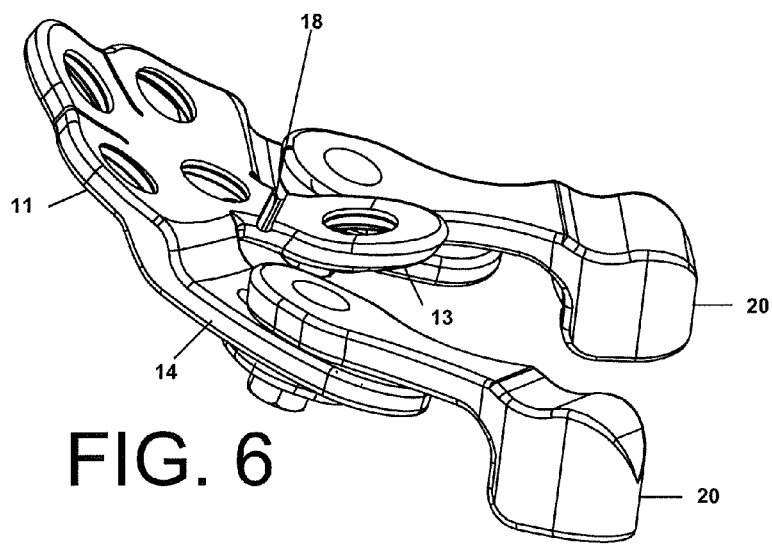
FIG. 6 is a perspective view of the assembled plate device of FIGS. 1-5 from the rear to illustrate the curvature of the plate member.

The occipital plate device of FIG. 1 can be seen in a perspective side view in FIG. 6. This view illustrates the shape of the plate member, which allows it to lie against the surface of the occipital region of the skull. The lower lobe 13 of the plate curves upward in order to lie against the skull, while the lateral arms 14 are canted downward and away from the skull to provide clearance for the receiving device arms 25 that are positioned between the plate arms 14 and the skull. A groove 18 is provided above the lower lobe 13 to facilitate bending of the lower lobe 13 for positioning against the surface of the skull.

Figure 7:
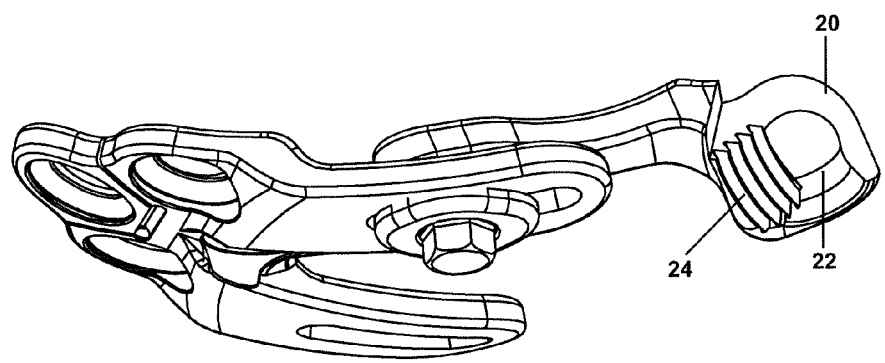
FIG. 7 is a partial cross sectional view of a rod receiving device coupled to a plate member.
Figure 8:
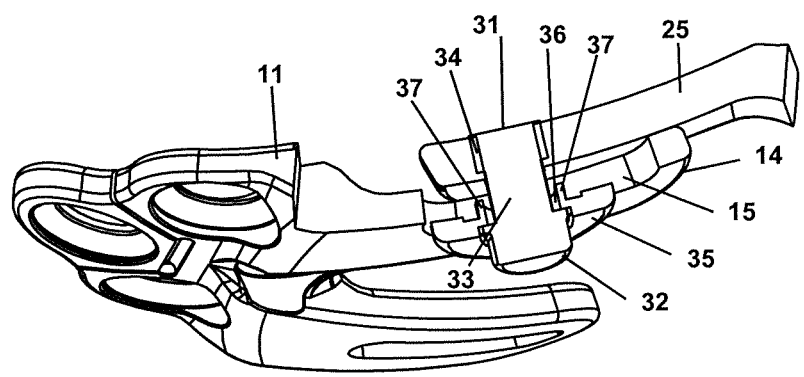
FIG. 8 is a partial cross sectional view of the slidable coupling elements of the device of FIG. 2.
Figure 9:
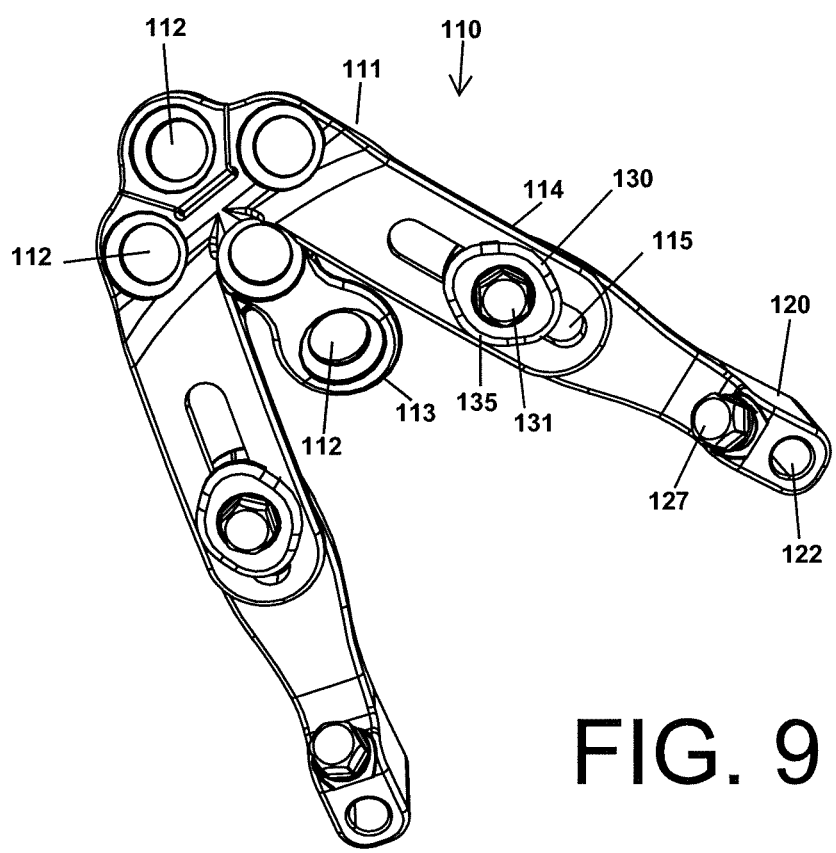
FIG. 9 is a perspective view of another adjustable occipital plate device wherein rods are received in set orientations with respect to rod receiving devices.
Figure 10:
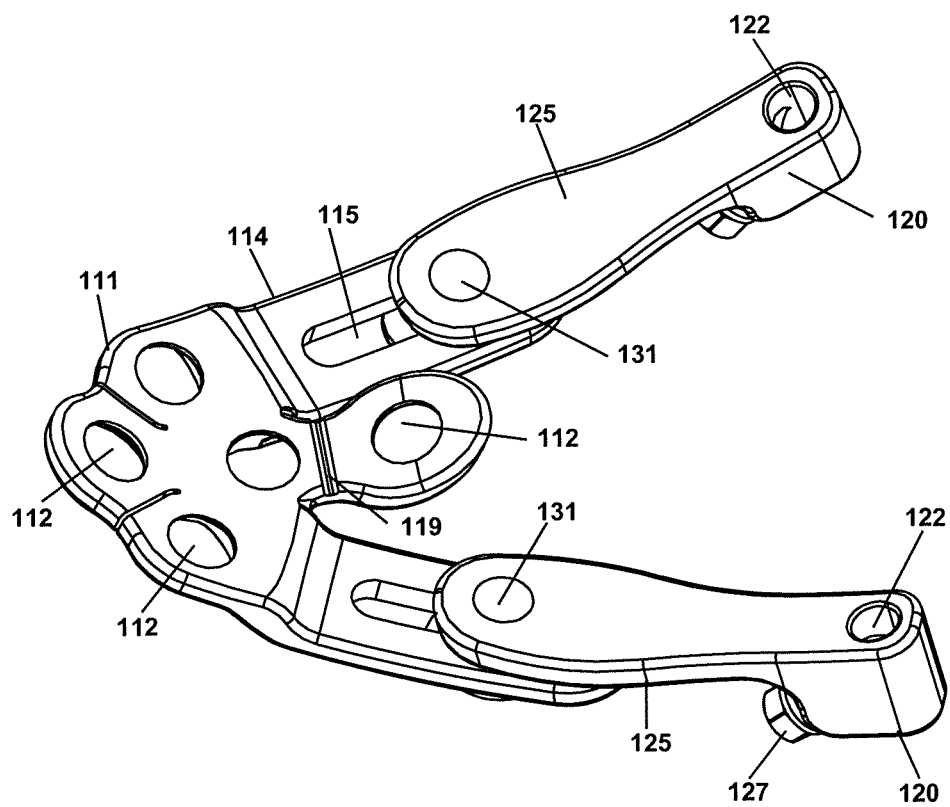
FIG. 10 is a perspective view of the device of FIG. 9 from the rear.
Figure 11:
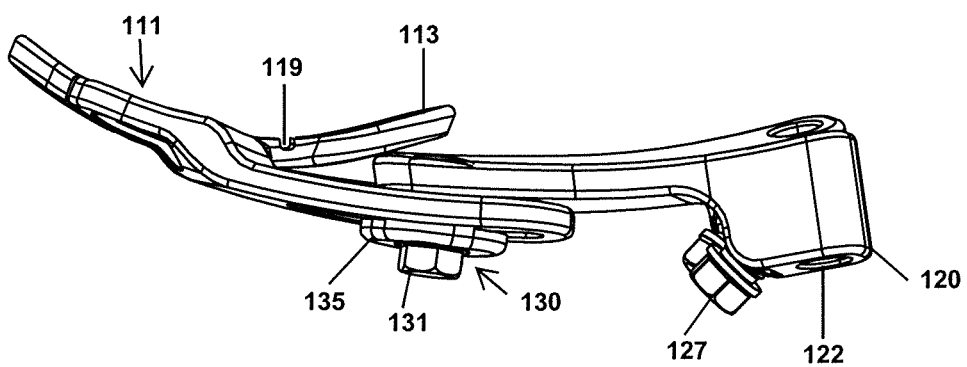
FIG. 11 is a side view of the device of FIG. 9.
Figure 12:
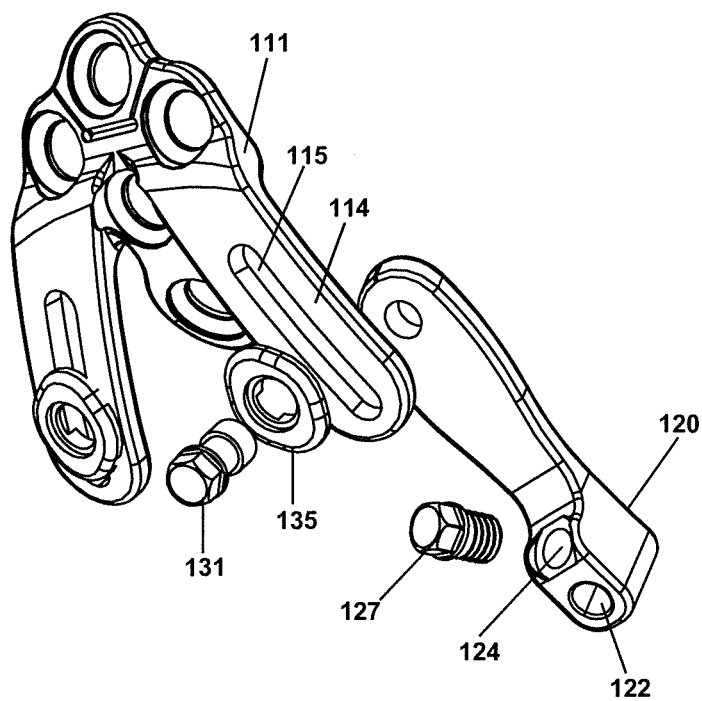
FIG. 12 is a perspective partially exploded view of the device of FIG. 9 illustrating the slidable members that couple the rod receiving device to the plate member.
Figure 13:
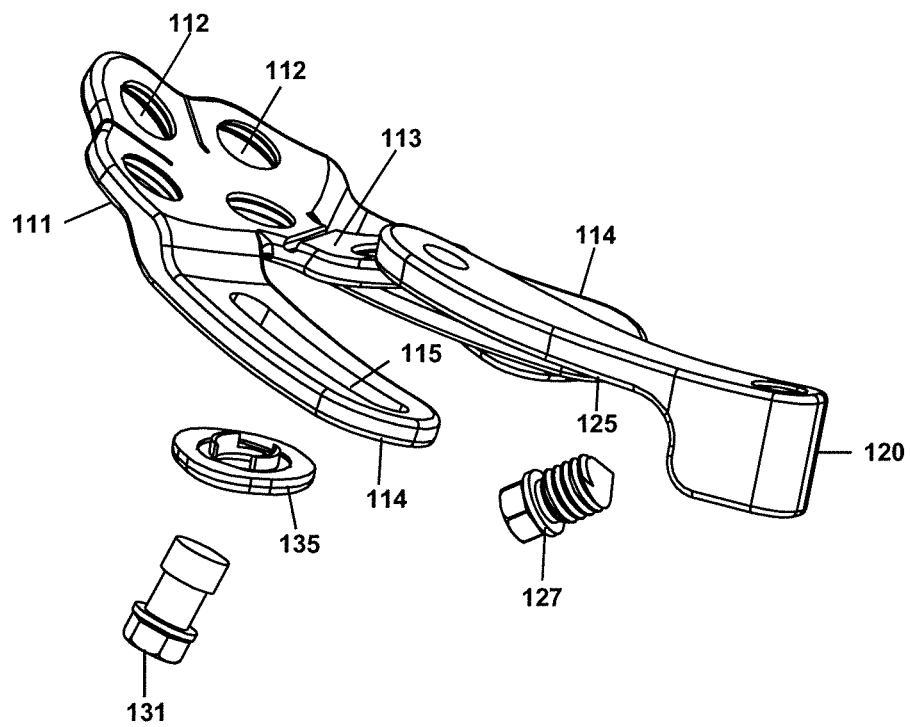
FIG. 13 is a perspective partially exploded view of the device of FIG. 9 from the rear illustrating the slidable members that couple the rod receiving device to the plate member.

A cross sectional view of the rod receiving device 20 is provided in FIG. 7. One side of one of the rod receiving members 20 is cut away to reveal the spherical cavity 22 and threaded aperture 24 therein. FIG. 8 provides a cross section of a portion of the plate arm 14 and the arm 25 of the rod receiving portion, illustrating how the two portions are coupled together. As previously described, a bolt 31 is disposed in an elongate aperture that forms a guide track 15 in the plate body 11. The enlarged head 32 of the bolt is nested on the sliding member 35 that slides along the guide track 15. The shank 33 of the bolt passes through the guide track 15, and a threaded portion 34 of the bolt is threaded into the arm 25 of the rod receiving portion. The head portion 32 of the bolt may be polygonal or otherwise shaped to facilitate turning with a wrench, nut driver, or other instrument. The turning of the threading of the bolt 31 relative to the rod receiving device arm 25 forces the bolt head 32 and the arm 25 against the lateral plate arm 14, clamping the plate arm 14 between the sliding member 35 and the rod receiving device arm 25. This clamping force creates friction that prevents the bolt 31 and the rod receiving device arm 25 from further movement along the guide track 15, and also prevents pivoting of the rod receiving device arm 25 about the bolt. The surfaces of the arms 25 and 14 may be roughened or otherwise contoured in order to enhance the locking force between the two when clamped together.

An alternative embodiment of an occipital plate device is shown in FIGS. 9-13. The embodiment illustrated in these figures is similar to the embodiment illustrated in FIGS. 2-8 except that the spinal rods are received in only one orientation rather than in a polyaxial manner. The illustrated device includes a relatively flat plate member 110 configured to be secured to the patient's skull, the plate member including a main plate body 111, two lateral plate arms 114, and a lower lobe 113 located between the lateral plate arms. Each of the main plate body and the lower lobe include a plurality of openings for bone screws designed to mount the plate member to bone. The plate member illustrated has a slight curvature to better match the surface of the occipital region of the skull than a flat plate.

In the device of FIGS. 9-13, rod receiving members 120 are coupled to the plate member 110 by a sliding pivot connector 130. As shown in FIGS. 3 and 4, the sliding pivot connector includes a bolt 131 and a sliding member or washer 135. As with other sliding members disclosed herein, the sliding members may be made of any suitably strong material, but are preferably made of a semi-flexible material such as nickel-titanium alloys (Nitinol) and other similar alloys. The bolts 131 each have an enlarged head 132 and a narrower shank portion 133 that is slidably disposed in the slot or guide track 115 of the plate's respective lateral arms 114 and connected to one of the rod receiving members 120.

Each of the spinal rods may pass fully through a bore 122 in its respective rod receiving member 120. The bores 122 are positioned to receive spinal rods in an orientation transverse to the surface of the plate body 111. A locking member 127 is received in an opening 124 of the receiving member and protrudes into the bore 122 from a transverse direction and applies force to each spinal rod in order to lock the rod in a fixed position within its respective rod receiving bore 122. The locking member 127 may be a threaded set screw or similar device, although the configuration of the locking member is not crucial as long as it is capable of engaging the rod receiving member 120 and securing a spinal rod therein.

The opening 124 for receiving the locking member should be formed to interlock with the locking member 127. For instance, the embodiment shown in FIG. 12 includes a threaded locking member 127 and a corresponding threaded opening 124 in the receiving member. When the locking member 127 is fully threaded into the receiving member 120, the leading end of the locking member presses against a rod that is disposed within the bore 122 of the receiving member, forcing the rod against the interior surface of the receiving device 120, applying frictional forces that prevent the rod from sliding through the bore 122. This provides the device and the spinal rods connected thereto with structural rigidity in order to partially or fully immobilize the skull and spinal column.

The locking members of FIGS. 9-13 have polygonal heads to facilitate manipulation with a wrench or nut driver, although locking members with internal drive recesses, as shown in FIG. 2, may alternatively be used. The locking members 127 may have a head portion of the same size and shape as that of the connecting bolt 131 of the slidable connector if desired, allowing manipulation of both types of members with the same tool.

The turning of the bolt 131 of the sliding pivot connector 130 in a first direction clamps the bolt head and an arm 125 of the rod receiving member against the plate lateral arm 114, locking the position of the two components relative to one another. The bolt 131 may be coupled to the receiving member arm 125 in any manner, including a threaded interface, welding, or a pivotable connection. Rotation of the bolt 131 in an opposite direction releases the clamping force between the rod receiving device arm 125 and the plate lateral arm 114, allowing the rod receiving device 120 to pivot about the bolt 131.

As in the previous embodiment, the sliding member 135 is disposed between the head 132 of the bolt and the plate arm 114, thereby acting as a washer and helping to secure the bolt 131. In addition, the sliding member also may extend into the arm guide track 115 in order to better guide the sliding pivot connector 130. For instance, the sliding member 135 may include projections 137 on the underside thereof that are fitted to be received in the guide track 115 of the plate arm 114.

As with the previous embodiment, the lower lobe 113 of the plate body 111, which is positioned between the lateral arms 114 of the plate, curves relative to the arms 114. The lower lobe 113 is configured to approximate the contour of the skull, maintaining contact with the bone while the arms 14 extend away from the skull at an angle. This configuration positions the rod receiving members 120 away from the skull to better receive the spinal rods connected to the spinal column. A groove 119 or the like may be provided to facilitate bending of the lower lobe or any other portion of the plate body 111.

In another aspect of the invention, a plate member 211 may be connected to a track member 250 to which a pair of rod receiving members or yoke members 270 are slidably connected, as shown in FIGS. 14-19. The sliding of the yoke members 270 along the track member 250 allows the distance between the yoke members to be adjusted so that the yoke members 270 may capture spinal rods having various orientations and distances from one another.

The track member 250 includes a guide slot or guide track 252 along its upper surface along which the yoke members 270 may slide. The yoke members 270 may be coupled to the track member 250 in a manner that allows for rotation and/or pivoting in one or more planes in addition to sliding in order to easily capture spinal rods positioned at various orientations.

For instance, the yoke members 270 each may be provided with a swivel base 280 mounted in the guide track 252, with the swivel bases configured to be coupled to the yoke members 270 in a manner that allows the yoke members 270 to be variously positioned. For instance, the swivel base 280 may allow the yoke member 270 to be rotated and/or pivoted in various planes in order to vary the orientation of the rod channel 275 in the yoke member.

Figure 14:
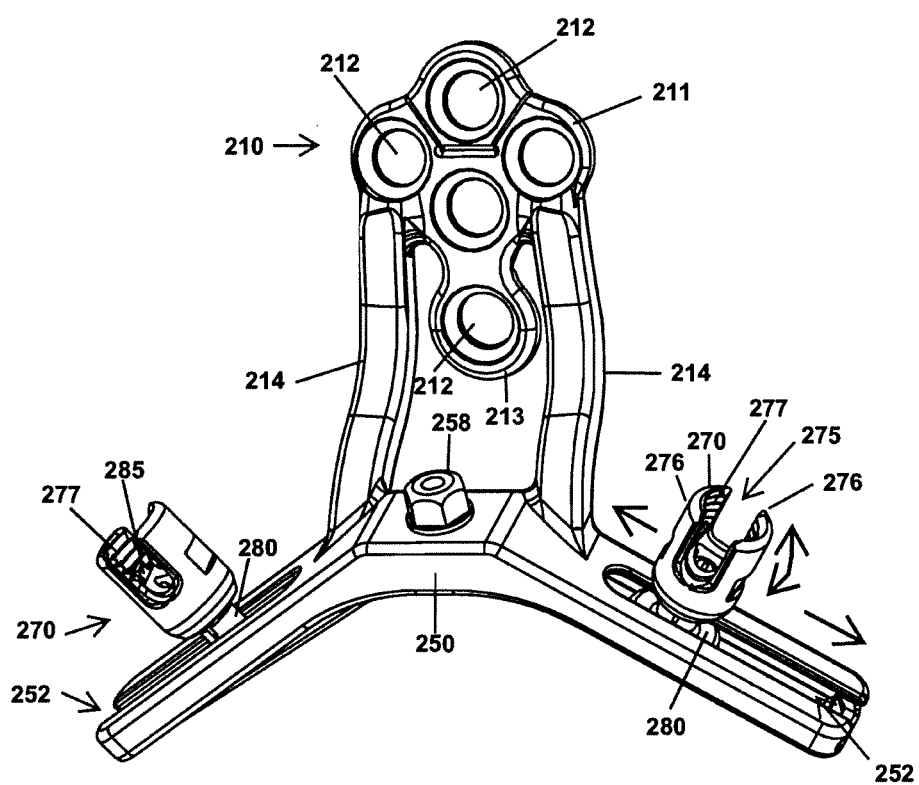
FIG. 14 is a perspective view of another occipital plate device including two slidable and polyaxial yoke members mounted to a track member that is coupled to a plate member.

The yoke members 270 illustrated in FIG. 14 are U-shaped members with upright arms 276 that form a channel 275 therebetween sized and shaped to receive a spinal rod. The bottom of the channel 275 may be rounded in order to cradle the spinal rod and provide line contact with the rod, or may alternatively be of another shape or configuration. The yoke members 270 also are configured to receive a locking member that secures a spinal rod within the channel 275. In the illustrated embodiment, the interior surface of the yoke members 270 are provided with threads 277 that interlock with complementary threads of set-screw type locking members. Alternatively, the yoke members may be configured to receive other type of locking members, such as an exterior nut. The yokes 270 also alternatively may be configured to receive various types of interior or exterior non-threaded locking members, including but not limited to bayonet-style locking members and the locking caps disclosed in U.S. Pat. No. 7,141,051; U.S. Published Application No. 2008/0045955; and U.S. Published Application No. 2007/0225711.

The yoke members 270 of the plate device 210 that secure the ends of the spinal rods may be of the same type provided for mounting to the vertebrae to secure other portions of the spinal rods, in order to allow for interchangeability of parts.

Alternatively, the yoke members may be of a different type with different locking members than are provided for securing the spinal rods to vertebrae.

Figure 15:
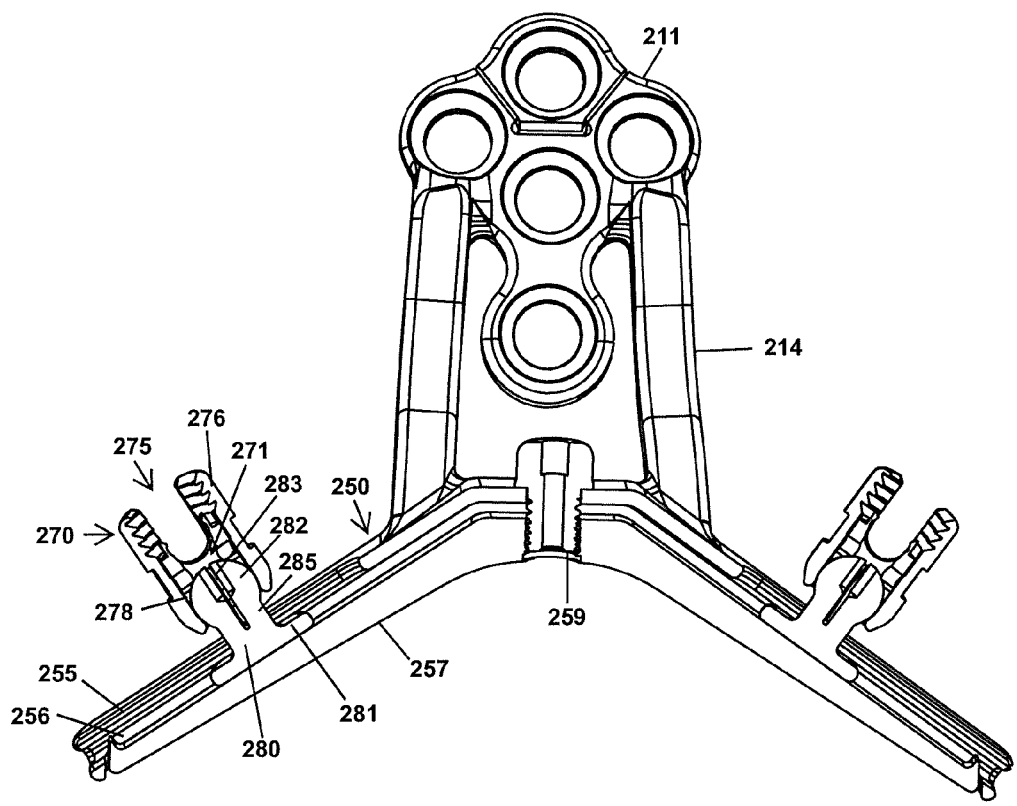
FIG. 15 is a cross-sectional view of the device of FIG. 14.

The swivel base 280 that couples the track member 250 to the yoke member 270 may have an enlarged portion disposed in a space 256 located below the guide track opening 255 of the track member, as best seen in the cross-sectional view of FIG. 15. This allows the swivel base 280 to translate along the guide track 255 without disengaging therefrom. In the illustrated device, the swivel base 280 includes an enlarged base portion 281 that is wider than the guide track opening 255. The base portion 280 is provided with clearance to translate through an open space 256 located below the guide track 255. The base portion is connected to a narrower neck portion 285 sized and configured to be slidably disposed through the guide track 255. A head portion 282 is connected to the neck portion 285 and serves as a coupling point for the yoke member 270.

The head of the swivel base advantageously may be partially spherical in order to allow the yoke member 270 seated thereon to pivot in a plurality of directions. Due to the size of the base portion 281 of the swivel base 280, the head portion 282 must be provided with a suitable means for insertion into the yoke member 270. For instance, in the illustrated embodiment the head portion 282 of the swivel base 280 is inserted into the yoke member 270 from below. In order to allow the head portion 282 to be inserted but inhibit it from backing out of the yoke member 270, the head portion 282 is provided with a compression gap 283 that allows the two halves of the head portion to deflect toward one another, reducing the width of the head and allowing it to pass through an opening in the lower portion of the yoke member 270.

Once the head member 282 is positioned inside the interior space 271 of the yoke member, the halves of the head will resiliently shift outward away from one another, returning to their original position. This resilient shifting of the halves of the head portion 282 provides a snap-lock connection between the swivel base 280 and the yoke member 270, coupling them together. At this point, a force must be applied to the head portion in order to force the halves of the head together to allow the head portion to escape through the lower opening of the yoke member. In order to prevent the escape of the head portion, a pin or wedge may be forced into the gap 283 between the head halves, forcing the halves of the head portion apart so that the overall profile of the head portion is too large to exit the yoke member 270.

If desired, the head portion of the swivel base 280 may be configured with multiple compression/expansion gaps, or may be initially sized to fit easily into the yoke member from below and then expanded by the insertion of a pin, wedge, or other expansion member that deforms the head portion and increases its diameter to a point that it cannot exit the yoke. Alternatively, other methods of positioning the head portion 282 within the interior space 271 of the yoke member 270 may be employed. For instance, the head portion may be provided as a separate component that is loaded into the yoke member 270 from the top and then connected to the neck portion 285 or base portion 281, such as through a threaded connection.

The interior space of the yoke member 270 includes a seat portion 278 that seats the lower portion of the swivel base head portion 282. The seat portion 278 of the yoke member may be curvate or semispherical in order to approximate the surface of the swivel base head portion 282, potentially providing multiple points of contact between the yoke member and swivel base. Alternatively, the seat 278 of the yoke member may have another shape, and may only contact the swivel base head portion 282 at distinct points if desired.

When the head portion 282 is spherical, as illustrated, the yoke member 270 may be tilted in any direction and rotated about its axis to align the channel 275 of the yoke along various axes to receive spinal rods of various orientations. Combined with the sliding movement of the swivel base 280 along the guide track 255, the yoke member 270 is provided with a wide variety of possible positions. Preferably, the neck portion 285 is sized and configured so as to provide the necessary strength to securely couple the track member 250 to the yoke member 270 while still allowing the yoke member 270 to tilt to a relatively large range of angles without interfering with the lower surface of the yoke member.

If desired, the head portion of the swivel base may be shaped to provide tilting of the yoke member 270 in only a set number of directions. For instance, the head portion may be cylindrical to provide size-to-side tilting of the yoke member 270.

The swivel bases 280 should be provided with a locking mechanism in order to lock their lateral positions and firmly hold spinal rods in place relative to the plate body 211. In the illustrated embodiment, the locking mechanism includes a locking plate 275 and a locking actuator 258. The illustrated locking actuator is a threaded bolt disposed in the track member 250 and threadably disposed in the locking plate 257 so that rotation of the bolt 258 in a locking direction draws the locking plate 257 upward toward the plate member 250. This upward movement of the locking plate 257 reduces the size of the space 256 below the track member 250, and clamps the base portions 281 of the swivel bases 280 between the locking plate 257 and the track member 250.

The clamping force of the locking plate 257 should be sufficient to prevent further translation of the swivel bases 280 along the guide track 255. Advantageously, the configuration of the illustrated locking plate allows for a single, centrally positioned locking actuator 258 to lock the positions of both swivel bases 280 simultaneously. Although shown as a bolt device, the locking actuator may be configured in a variety of ways, including but not limited to various rotatable on non-rotatable non-threaded devices, for instance a bayonet style mechanism with angled flanges or slots paired with complementary structures in the locking member 257 and/or the track member 250.

The locking actuator may be provided with a mechanism that prevents it from separating from the locking plate. For instance, an anti-backout pin 259 may be coupled to the actuator 258 and configured to abut the bottom of the locking plate 257 to prevent the actuator from exiting out of the top end of the locking plate. The anti-backout pin 259 may be configured to be snap-locked into a bore of the actuator 258, or may be coupled thereto by welding or other means.

Figure 16:
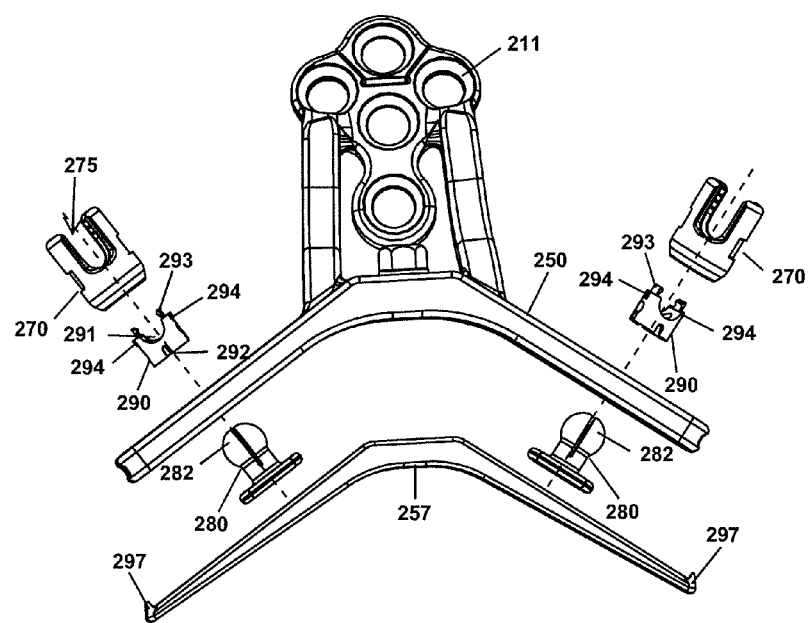
FIG. 16 is an exploded view of the device of FIG. 14.
Figure 17:
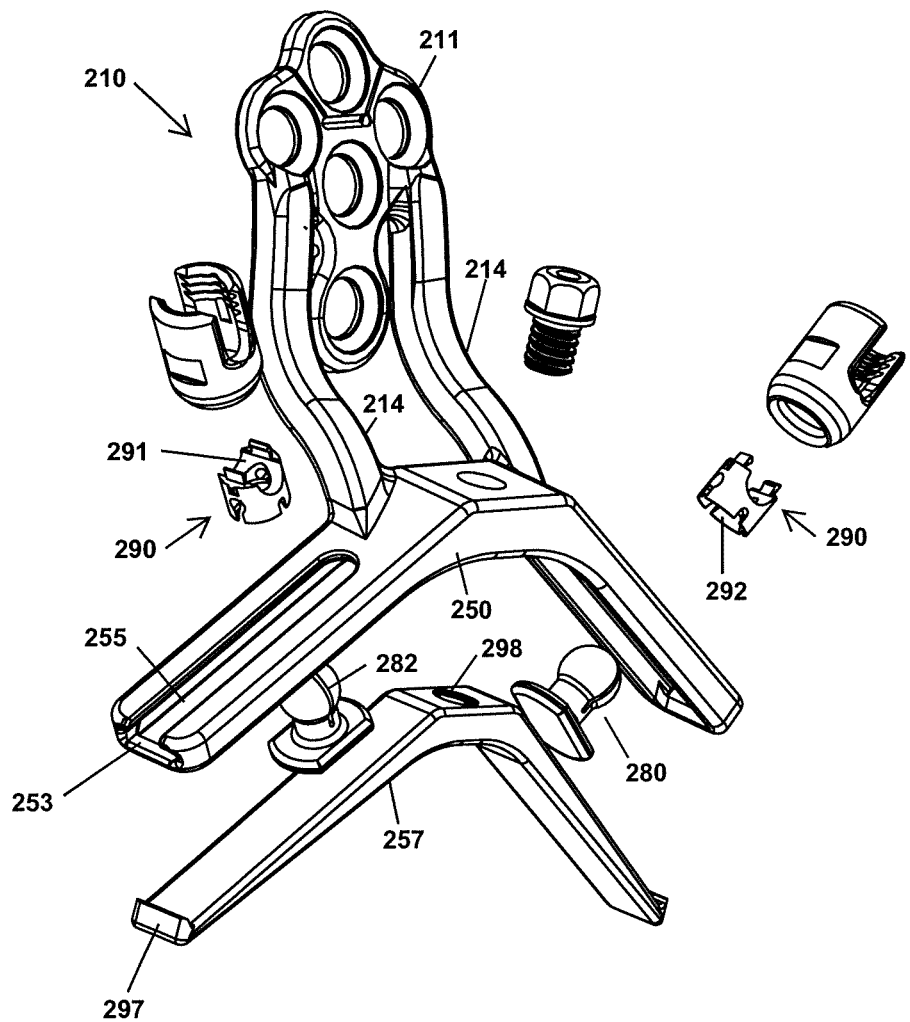
FIG. 17 is a perspective exploded view of the device of FIG. 14.

The moving parts of the plate device of FIG. 14 can best be seen in the exploded view of FIGS. 16 and 17. FIG. 16 shows a front exploded view, where the locking member 257 and track member 250 are separated, with the swivel bases 280 therebetween. Stop limits 297 are provided at each end of the locking plate 257 in order to prevent the swivel bases 280 from exiting the lateral ends of the guide tracks when the device is assembled. The yoke members 270 are shown in FIG. 16 separated from the head portions 282 of the swivel bases 280. In addition, insert members 290 are shown for each yoke member. The insert members are configured to sit atop the head portions 282 of the swivel bases 280 and assist in locking the angular orientation of the yoke members 270.

Locking of the position of the yoke members may be accomplished in several different ways. The illustrated yoke members 270 are designed to lock to the generally spherical swivel base heads 282 at a set orientation by placing a downward force on the head portion (and a relative upward force on the yoke member 270) that presses the head portion 282 into the seat portion 278 of the interior of the yoke member, using friction to prevent further tilting or rotation of the yoke member 270 relative to the head portion 282. When a yoke member is positioned at a desired angle and a spinal rod is received in the channel 275 of the yoke, a locking member may be inserted on top of the rod to close off the upper end of the channel. Preferably, this locking member applies a downward force upon the rod disposed in the channel, which then in turn transmits the force downward upon the swivel head portion 282 to lock it against the interior of the yoke member. The locking force may be transmitted from the spinal rod to the swivel base head portion 282 directly or through a compression member, such as the illustrated insert member 290. The insert member provides more surface contact with the head portion 282 compared to the spinal rod alone.

The illustrated insert member 290 includes a concave upper surface 291 for seating the rod and a spherical lower surface 292 for seating upon the swivel base 280. The insert member 290 also may include rod receiving arms 293 on its upper surface in which the spinal rod may be snap-locked prior to full locking of the yoke member 270. The exterior of the insert member 290 may be equipped with wings 294 or other structures to guide the orientation of the insert 290 as it is disposed within the yoke member 270 so that the concave upper rod seating surface 291 and the channel 275 of the yoke member are properly aligned. In addition, the wings 294 may snap-lock within the interior of the yoke member 270 so that the insert 290 exerts a compression force upon the swivel head portion 282 even prior to introduction of the spinal rod and locking member into the yoke member 270. Configuring the insert member 290 in this manner allows the yoke member 270 to be rotated and tilted to a desired position and then provisionally locked in place prior to aligning the spinal rod with the yoke member.

A perspective exploded view of the occipital plate device 210 of FIG. 14 is shown in FIG. 17. The guide tracks 255 are shown to have open ends 253 that allow the swivel bases 280 to be slid into the guide tracks from the sides during assembly. Alternatively, the swivel bases 280 may have head portions sized to pass through the guide tracks 255 from below. When the locking plate 257 is assembled with the track member 250, the swivel bases 280 are prevented from exiting the openings 253 by the stop limits 297 of the locking plate 257. From this view, the curvature of the arms 214 that connect the track member 250 to the plate member 211 may be seen. The arms 214 are curved so that when the plate member 211 is mounted to the occipital region of the skull, the arms 214 hold the track member 250 away from the skull and toward the spine, positioning the yoke members 270 above the vertebrae to which spinal rods are secured. This positions the yoke members 270 so that they may receive spinal rods that are closely mounted parallel to the spine without requiring the rods to be bent outward away from the spine.

Figure 18:
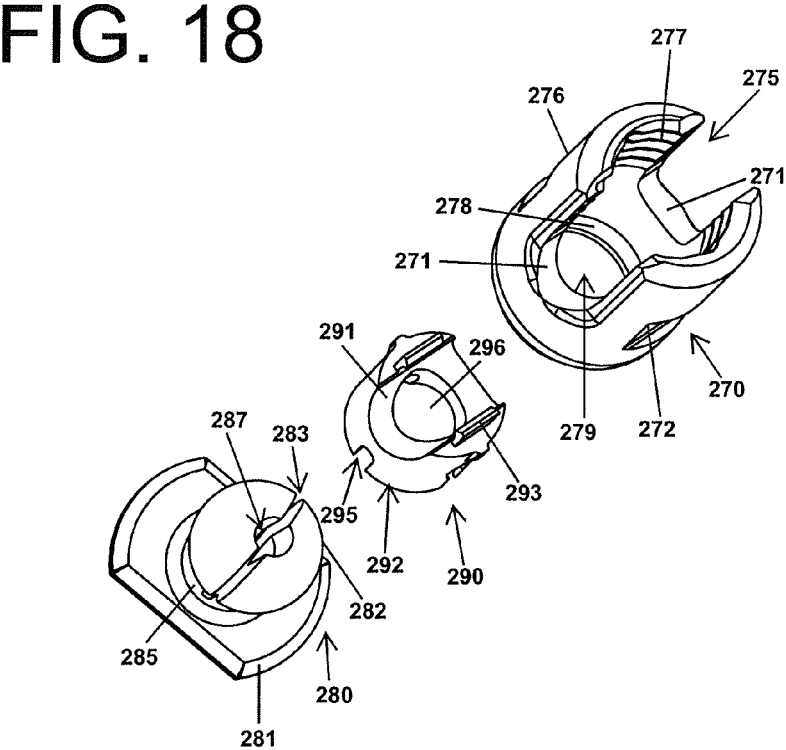
FIG. 18 is an exploded view of the yoke member and associated swivel base illustrated in FIG. 14.

The yoke 270, swivel base 280, and insert member 290 are shown in detail in FIG. 18 in a magnified exploded perspective view. As previously indicated, the yoke member may include opposed upright arms 276 that form a channel 275 therebetween for receiving a spinal rod or other elongate member. A seating surface 271 may be provided at the bottom of the channel 275. A seating surface 278 at the bottom of the yoke member interior may be provided for seating the head portion 282 of the swivel base 280. An opening 279 at the bottom of the yoke member 270 allows the swivel base 280 to be inserted into the yoke member 270, and the opening 279 is preferably sized and configured to snap-lock with the swivel base head portion 282.

The insert member 290 for the yoke member 270 is shown as generally cylindrical to generally match the interior of the yoke member 270. Although this is not necessary, in some instances it is advantageous for the insert member to fit snugly in the interior of the yoke member 270, such as when it is desired for the insert member 290 to achieve provisional locking of the swivel base 280 relative to the yoke without the insertion of the spinal rod and a rod locking member. The insert member upper surface may be concave as shown in order to seat the rod thereagainst with line contact, reducing stress risers on the rod, but other configurations are also possible. Flexible arms 293 may also be provided to receive the spinal rod and hold it against the upper surface 291 of the insert member. Slits 295 may be provided in the insert in order to allow the insert member 290 to deform slightly as pressure is applied and the member is compressed on the swivel base head portion 282.

In order to couple the yoke member 270 to the swivel base, the head portion 282 of the swivel base is inserted through the lower opening 279 of the yoke member. The slit 283 allows the head portion 282 to compress in order to fit through the opening 279. Once fully inserted into the yoke member interior, the head portion 282 either resiliently springs back to its original shape, or is splayed by inserting a wedge member into the slit 283. Preferably, even if the head 282 resiliently returns to its original width after insertion into the yoke member a wedge, pin, or similar member is inserted into the head portion 282 in order to prevent the head portion from later collapsing and exiting the yoke member. In the illustrated embodiment, the head portion 282 includes a cylindrical opening 287 for the insertion of a pin.

After the swivel base 280 is coupled to the yoke member 270, the yoke member may be swiveled to a desired orientation by rotation and/or pivoting of the yoke member 270 about the head portion 282 of the swivel base 280. The ease with which the yoke member 270 swivels will be in part determined by the tightness of the fit between the swivel base head portion 282 and the interior of the yoke member. If the two members fit tightly together, some amount of friction will be required to rotate and pivot the yoke member 270, which may be advantageous in certain situations since it reduces accidental movement of the yoke member.

The insert member 290 may be inserted into the top of the yoke member 270 either before or after the insertion of the swivel base 280. An opening or bore 296 passing through the insert may be provided in order to allow manipulation of the swivel base 280 after the insert member 290 is disposed in the yoke member. For instance, the bore 296 through the insert member allows access to the cylindrical opening 287 of the swivel base for inserting a wedge member therein. When the insert member is introduced into the yoke member, the concave upper surface 291 of the insert member should be properly aligned with the channel 275 of the yoke formed by the upright arms 276 in order to allow the assembly to properly receive a spinal rod. Wings 294, grooves, or other structures may be provided in order to maintain proper alignment of the insert member. As can be seen in FIG. 18, corresponding structures may also be provided on the interior surface of the yoke, such as the grooves that traverse the threading 277 on the interior of the yoke arms 276. The rod may be seated on both the concave surface 291 of the insert member and the concave seating surface 271 of the yoke member, or only on the surface of the insert with a clearance between the rod and the yoke seating surface 271. Alternatively, the rod may be seated only on the seating surface 271 of the yoke, or the assembly may be designed without an insert member so that the rod presses directly against the head 282 of the swivel base 280.

When a spinal rod is positioned in the channel 275 of the yoke member, downward force applied to the rod forces the insert member 290 disposed below the rod into contact with the swivel base 280. One or more slits 295 may be provided in the insert member 290 so that the insert may deform slightly as it is compressed onto the swivel head portion 282. To secure the spinal rod within the yoke channel 275, a locking member may be provided that blocks the upper end of the channel and maintains a downward force upon the rod, which transmits the force to the insert member 290, which compresses against the swivel head portion 282 and forces it against the seating surface 278 of the yoke member, frictionally locking the position of the swivel base 280 and the yoke 270 relative to one another. The locking member should be designed to engage the yoke 270 so that it is capable of holding the spinal rod in the channel 275. For instance, the illustrated yoke 270 has interior threads 277 configured to receive a set screw by rotational insertion. Recesses 272 may be provided in the exterior of the yoke member in order to provide a gripping surface for holding the yoke in place while the locking member is engaged.

As an alternative to a set screw locking device, the yoke 270 may be configured to receive other types of locking caps, such as the non-threaded locking caps disclosed in U.S. Pat. No. 7,141,051; U.S. Published Application No. 2008/0045955; and U.S. Published Application No. 2007/0225711. The yoke member 270 and its corresponding locking member may be the same as or different than the coupling members used to secure other portions of the spinal rods to the vertebrae of the patient.

Figure 19:
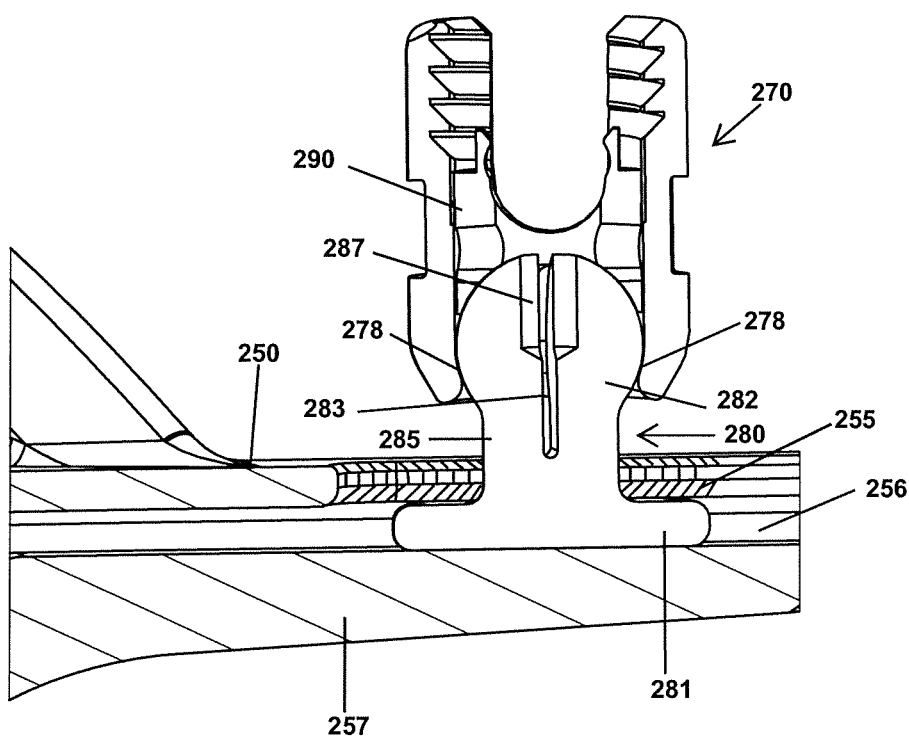
FIG. 19 is a cross-sectional view of the yoke member and associated swivel base illustrated in FIG. 14 slidably mounted in a guide track of the device.

The assembled yoke member 270 and swivel base 280 are illustrated in the cross sectional view of FIG. 19. The base portion 281 of the swivel base 280 is clamped between the locking plate 257 and the track member 250, with the neck portion 285 and head portion 282 protruding from the guide track 255 of the track member. The yoke member 270 is pivotably mounted to the head portion 282 of the swivel base, which is seated against the interior seating surface 278 of the yoke member. The insert member 290 is disposed in the interior of the yoke member and seated on top of the swivel base 280.

Figure 20:
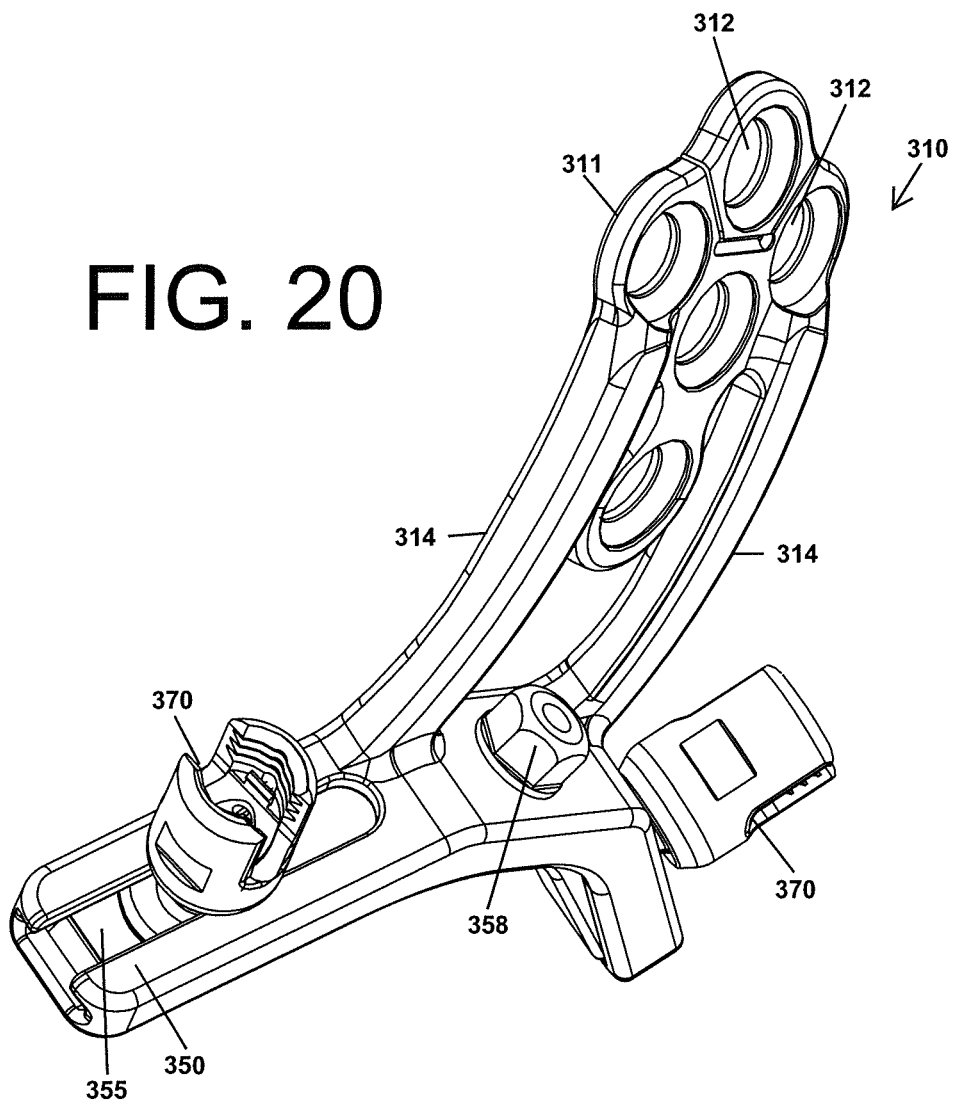
FIG. 20 is a perspective view of a plate device similar to that shown in FIG. 14.
Figure 21:
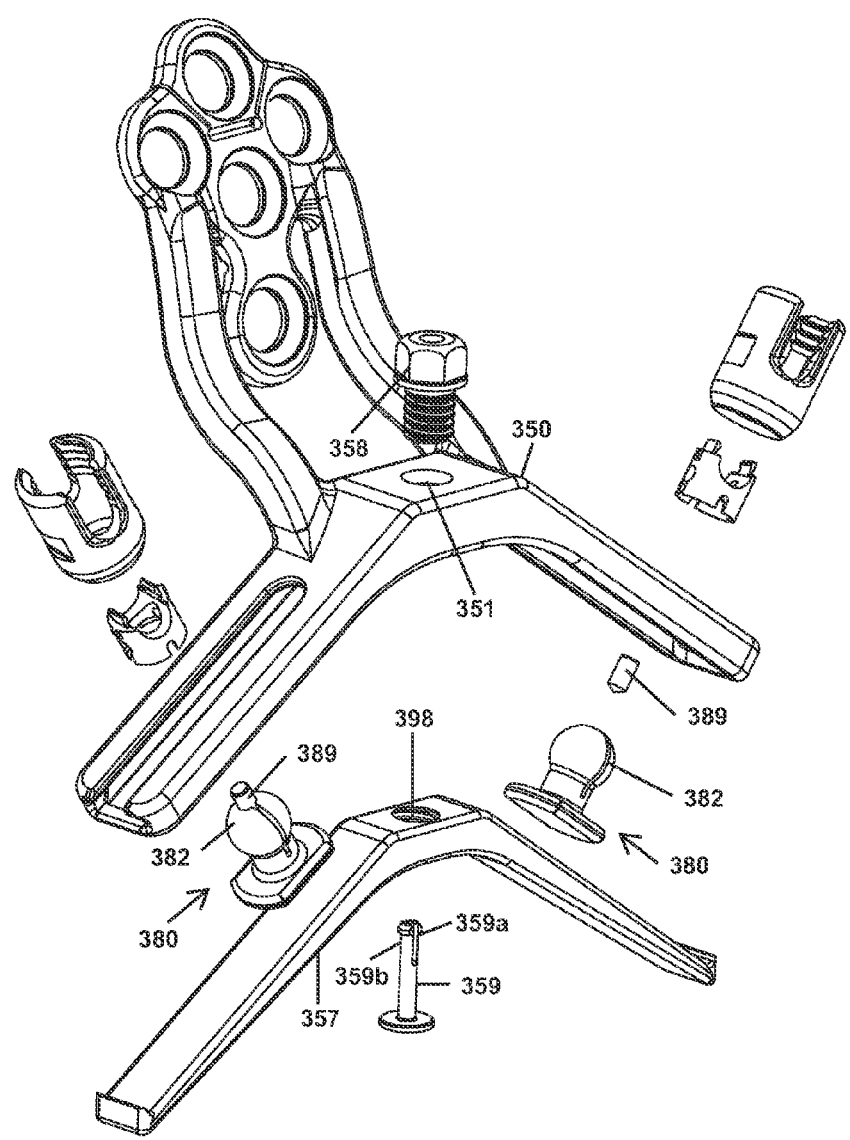
FIG. 21 is an exploded view of the plate device of FIG. 20.

A similar occipital plate device 311 is illustrated in FIGS. 20 and 21, and includes a pair of yoke members 370 slidably and pivotably coupled to a guide track 355 of a track member 350 that is mounted to a plate body 311 having a plurality of openings 312 for anchor devices such as screws. As can be seen, the arms 314 that connect the track member 350 to the plate member 311 are of a different shape than provided in the previous embodiment, and serve to hold the track member 350 closer to the skull when the plate member 311 is mounted to the occipital region of the patient's skull.

As with the previous embodiment, the device shown in FIGS. 20-21 includes a single actuator 258 to selectively inhibit lateral and medial translation of the yoke members 370. The exploded view of FIG. 21 also shows pin members 389 that are insertable into the head portions 382 of the swivel bases 380 in order to prevent compression of the head portions and maintain positioning of the head portions 382 within their respective yokes 370. If desired, the head portions 282 and pins 389 may be configured so that the pins splay the halves of the head portions 382 when inserted to an extent that causes frictional engagement between the exterior of the head portions 382 and the interior surfaces of their respective yoke members 370.

Also illustrated in FIG. 21 is the anti-backout pin 359 that maintains the coupling between the locking actuator 358 and the locking plate 357. The actuator 358 is disposed in an opening 351 at the center of the track member and then threaded into a threaded aperture 398 of the locking plate. Advancing the threads of the actuator 358 through the threaded aperture 398 pulls the locking plate 357 upward in order to clamp the swivel bases 380 against the track member 350. The anti-backout pin 359 includes two gripping members 359a and 359b configured for one-way linear insertion into an axial bore of the actuator 358. The leading surfaces of these gripping members are sloped in order to force the members to compress together when inserted into the actuator 358 in a forward direction, but once inserted past a widened portion of the interior of the actuator the gripping members 359a and 359b spring apart. The trailing ends of the gripping members are shaped to prevent backward translation of the anti-backout pin 359. Once coupled to the actuator, the enlarged base of the anti-backout pin 359 prevents the locking plate 357 from separating from the actuator 358.

Another example of a highly adjustable occipital plate device 401 is shown in FIGS. 22 through 26. The device 401 includes a plate member 410 with a plurality of holes for receiving anchor members, a pair of telescoping arms 430 pivotably mounted to the plate member 410 by a swivel connection 420, and rod receiving heads 440 and 460 mounted to the telescoping arms.

The telescoping arms 430 each include a housing portion 431, an inner arm 435, and a length adjusting member 437. The inner arm 435 is configured to translate and rotate with respect to the housing member 430, allowing for the length and orientation of the arm 430 to be adjusted. When the desired length and orientation is achieved, the length adjusting member 437 may be actuated in order to set the position of the inner arm 435 relative to the housing 430. The length adjusting member 437 may be a set screw or other device capable of clamping the inner arm 435 to the interior of the arm housing 431 in order to inhibit relative movement of the components of the telescoping arm assembly 430.

Figure 22:
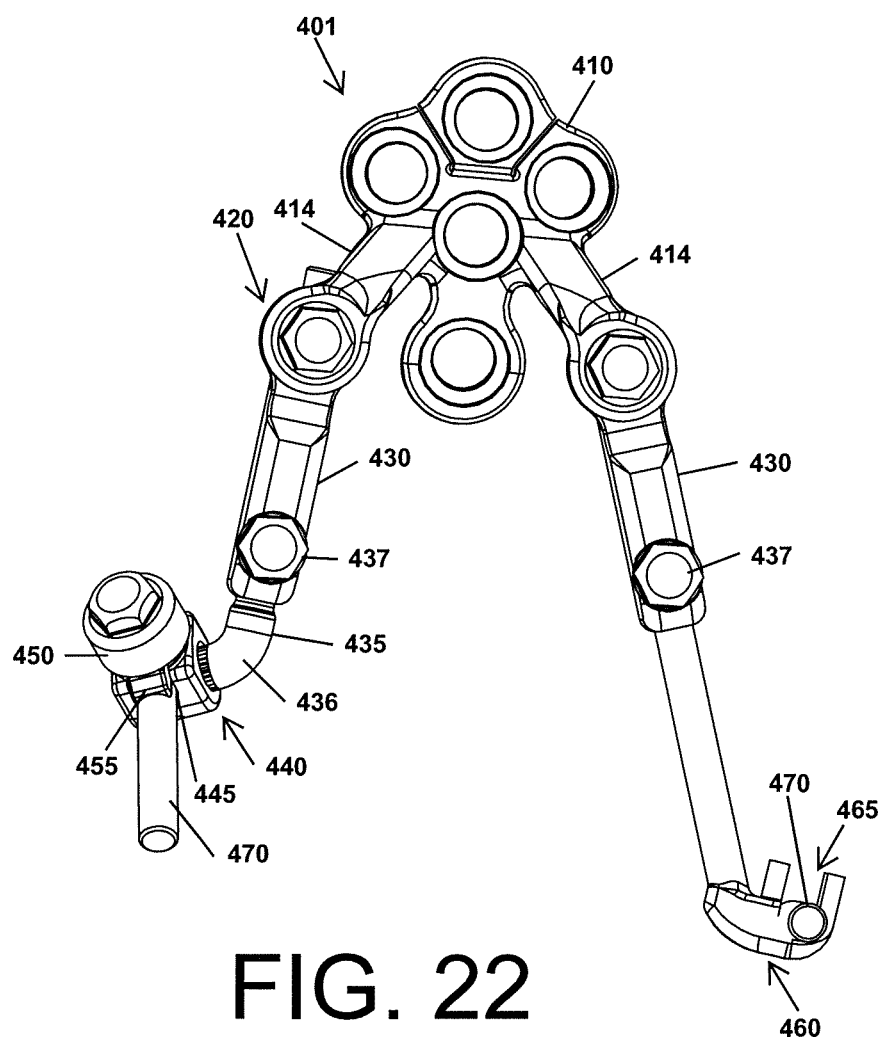
FIG. 22 is a perspective view of a multi-articulated plate device for securing spinal rods including telescoping rod receiving members.

In FIG. 22, two different types of rod receiving heads are shown. The fixed rod receiving head 460 on the right hand side of the device does not pivot or rotate with respect to the telescoping arm and has a channel 465 to receive a spinal rod 470. The channel 465 may be closed off by the attachment of a locking cap to the rod receiving head 460. The locking cap may take various forms.

The variable rod receiving head 440 on the left of the device is coupled to an elbow joint 436 of the inner arm 435 of the telescoping assembly 430, and is able to rotate thereabout. A channel 445 is provided in the head 440 to receive a spinal rod 470. The spinal rod 470 may be locked into place in the rod receiving head 445 by a locking cap 450, which may be rotatably coupled to a wedge plate 455 that is positioned adjacent to the spinal rod 470.

Figure 23:
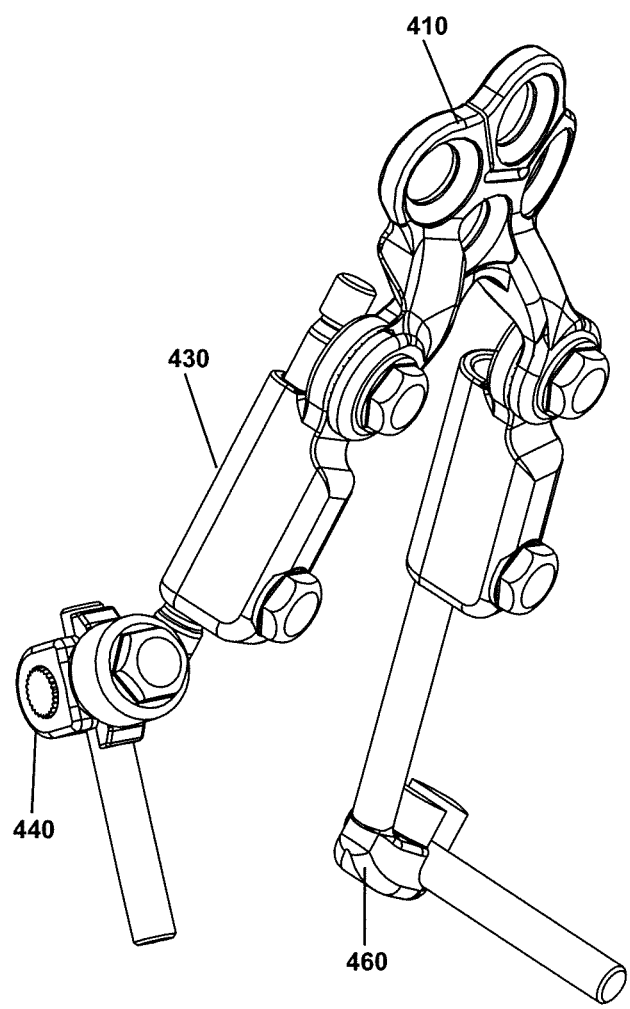
FIG. 23 is a side perspective view of the device in FIG. 22.
Figure 24:
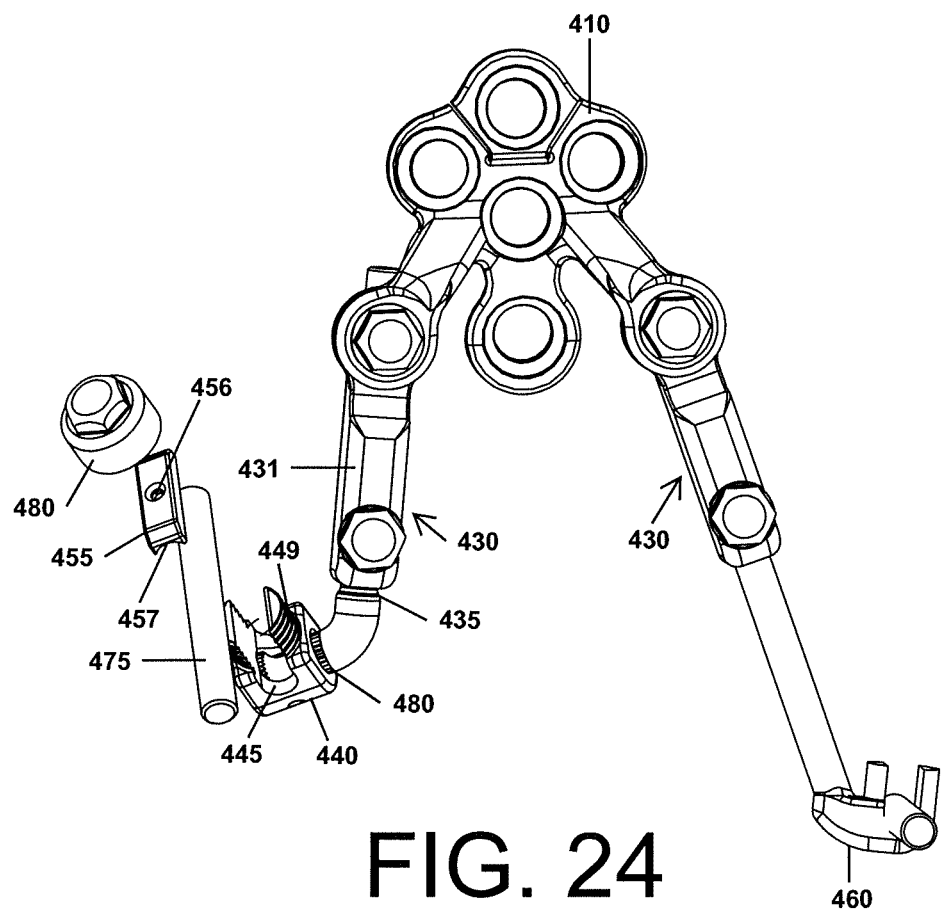
FIG. 24 is a front view of the device of FIG. 22 with the locking cap and spinal rod removed from one rod receiving device.

A perspective view of the device is shown in FIG. 23, illustrating the positioning of the telescoping assemblies 430 relative to the plate member 410. FIG. 24 illustrates the telescopic adjustment of one of the telescoping arm assemblies 430, positioning the fixed rod receiving head 460 further away from the plate member 410. The locking cap 450 is shown disengaged from the variable rod receiving head 440, allowing the spinal rod 470 to be removed therefrom. Threading 449 is provided about the upper portion of the variable rod receiving head 440 in order to secure the locking cap 450 by rotational locking of threads on the interior of the locking cap 450 and the threading 449 on the rod receiving device. A wedge plate 455 may be provided for placement between the locking cap 450 and the surface of the spinal rod 470. The illustrated wedge plate 455 includes a concave recess 457 on the underside of the plate to mate with the surface of the rod 470, and also includes an optional coupling feature 456 for rotatably coupling the plate 455 to the underside of the locking member 450, such as by a post or pin received in the coupling feature 456.

Figure 25:
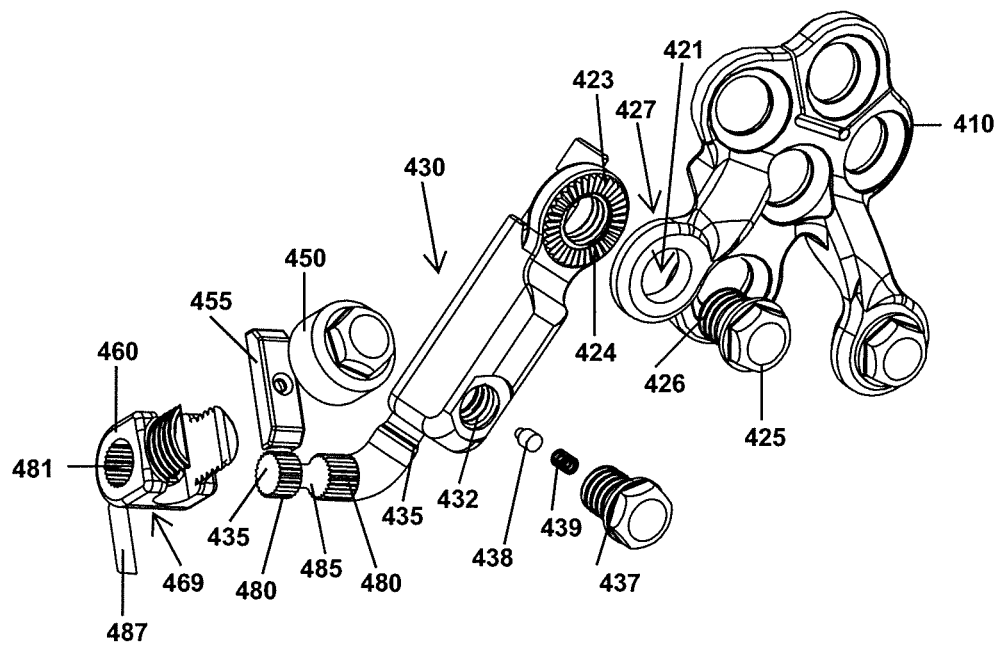
FIG. 25 is a perspective partially exploded view of the device of FIG. 22.
Figure 26:
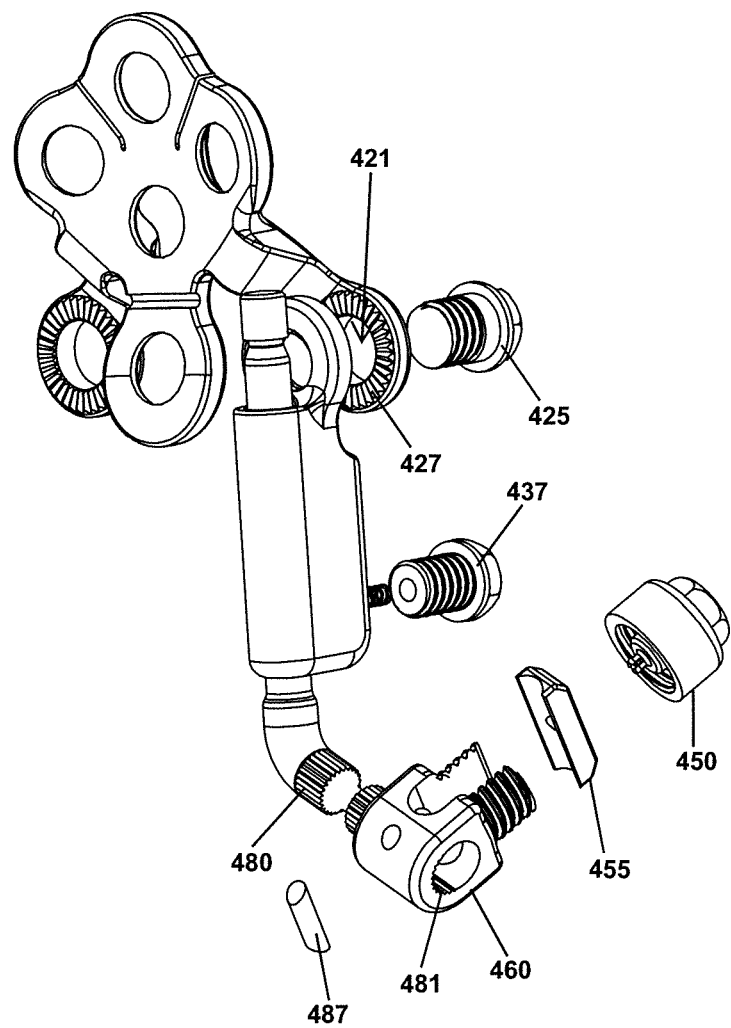
FIG. 26 is a perspective partially exploded view from the rear of the device of FIG. 22.
Figure 27:
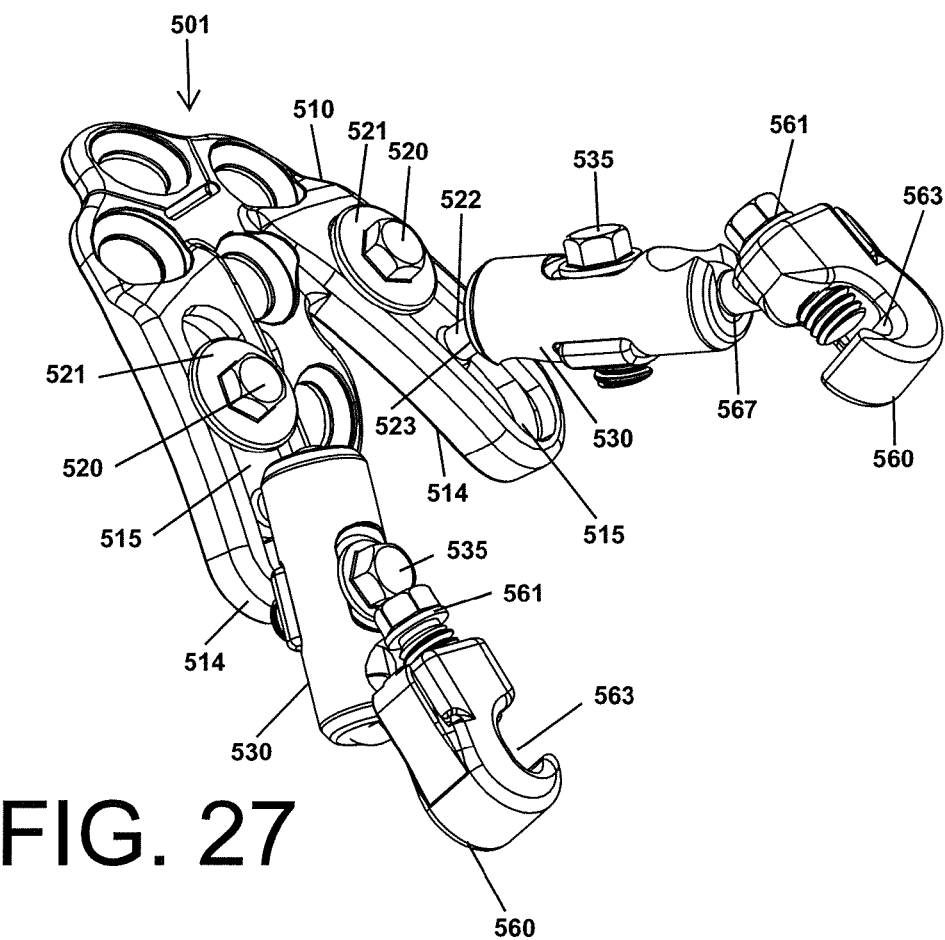
FIG. 27 is a perspective view of a multi-articulated plate device having arms with a plurality of ball-and-socket connections slidably mounted to a plate member.
Figure 28:
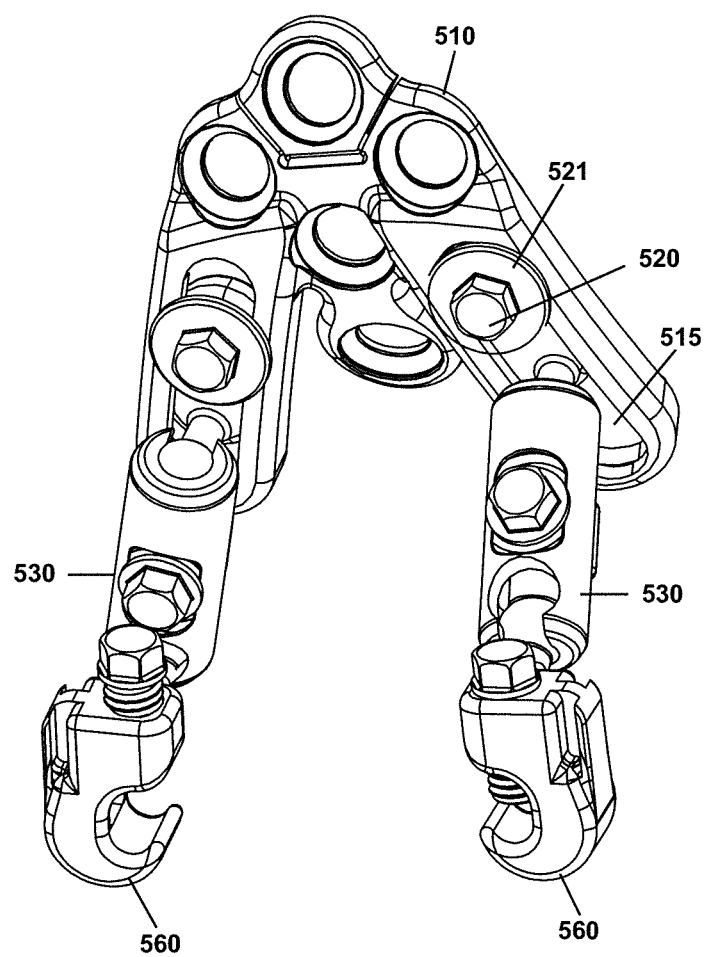
FIG. 28 is a perspective view of the device from FIG. 27 from above.

The telescoping assembly 430 is shown partially disassembled in FIGS. 25 and 26 in order to better show its relationship to other portions of the device. FIG. 25 illustrates a perspective view of the device from the front (the side that faces away from the skull when mounted), whereas FIG. 26 shows a perspective view of the device from the rear (the side that is placed adjacent the skull for mounting).

The annular array of teeth 480 provided around a portion of the inner arm 435 is designed to interact with complementary teeth 481 disposed on an interior surface of the adjustable rod receiving head 440 in order to facilitate gripping of the inner arm by the receiving head. When a clamping force is applied to a spinal rod received in the receiving head 440 by the locking member 450, the inner arm 435 is pushed downward relative to the receiving head 440 and the receiving head 440 is pulled upward relative to the inner arm 435, meshing teeth 480 together with teeth 481 to inhibit rotational movement of the receiving head 440 about the inner arm 435. Until the locking cap 450 is secured to the receiving head 440, however, the receiving head may be rotated forward and backward to align the channel 445 for receiving the spinal rod as desired relative to the plate member. In the middle of the toothed region 480 of the inner arm 435 is an annular recess 485. The spinal rod captured by the rod receiving head will be seated against this annular recess when fully seated. In addition, a pin 487 is provided that may be inserted into the rod receiving head 440 through a bore 449 in the side of the receiving head. When inserted, the pin lies in the underside of the annular recess 485, on the opposite side of the annular recess that the spinal rod rests against, and prevents the rod receiving head 440 from shifting from side to side along the inner arm 435. In this manner, the receiving head 440 is prevented from sliding off of the inner arm 435.

The length adjusting member 437 may be a bolt or other similar device that acts to clamp the sliding inner arm 435 in place within the housing member 341 of the telescoping arm assembly 430. The illustrated length adjusting member 437 is a threaded bolt that advances through a threaded opening 432 in the housing 431 upon rotation. A plunger 438 and spring 439 are provided for insertion into the bolt 427, and exert a moderate amount of pressure against the inner arm 435 even when the bolt 427 is not tightly clamped. The plunger thereby biases the inner arm 435 from freely sliding through the housing 431. In addition to telescopic sliding, the inner arm 435 may be rotated to adjust the position of the rod receiving head 460, swinging the head forward and backward out of the plate of the plate member 410.

The telescoping arm assembly 430 may also be adjusted by pivoting the arm about a swivel connection 420 that couples the arm 430 to the plate member 410. The pivoting of the arm 430 shifts the rod receiving head laterally outward or medially inward. The pivoting of the arm is provided by a bolt 425 or other member that passes through an opening 421 in the plate member 410 and is coupled to the telescoping arm. In the illustrated embodiment, the bolt 425 may be threadably coupled via its threaded shank 426 to a threaded aperture 424 attached to the telescoping arm assembly 430. Tightening of the bolt 425 clamps a portion of the plate member 410 between the telescoping arm 430 and the head of the bolt 425, inhibiting movement therebetween. A circular array of teeth 423 may be provided around the threaded opening 424 in order to assist in preventing movement of the arm by meshing with complementary teeth 427 surrounding the opening 421 on the back surface of the plate member 410. The meshing of the teeth when a clamping force is exerted by the bolt 425 is much more effective for resisting pivotal movement of the arm 430 than reliance solely on friction between relatively flat surfaces.

Another mechanism for adjusting the positioning of rod receiving devices relative to a plate member is shown in FIGS. 27 through 33. The plate device 501 includes a pair of elongate guide tracks 515 in arm portions 514 of the plate member 510. Sliding members 522 are disposed in the guide tracks, and are configured to slide therealong. A locking member 520 inhibits movement of the sliding member 522 by clamping the sliding member against the perimeter of the guide track 515 of the plate body 510. A sliding washer member 521 assists in locking the sliding member 522 in place.

Articulating arms 530 are coupled to the plate member 510 through the sliding members at ball and socket connections 523 and serve to position rod receiving head members 560 configured to clamp to spinal rods or other elongate members. In the illustrated embodiment, the receiving head members 560 include arcuate recesses 563 configured to cradle spinal rods, and a set screw clamping member 561 disposed in the head member 560 and positioned to clamp the spinal rod against the arcuate recess 563 when rotationally advanced.

The articulating arms 530 of the device 501 are provided with a plurality of articulating ball and socket connections for each arm because they are joined to both the plate member 510 and the rod receiving heads 560 by ball and socket connections. A single actuator 535 simultaneously locks both ball and socket connections 523 and 567 against movement, as will be described below.

Figure 29:
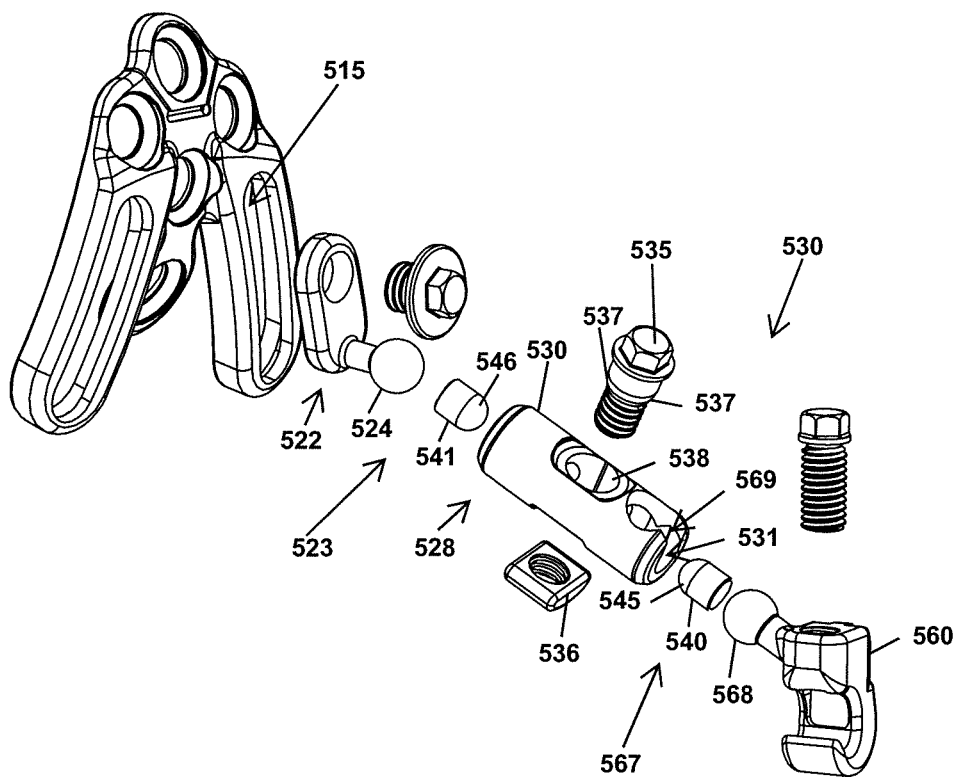
FIG. 29 is a partially exploded view of the device of FIG. 27 showing the components of the slidably mounted multi-articulating arms.
Figure 30:
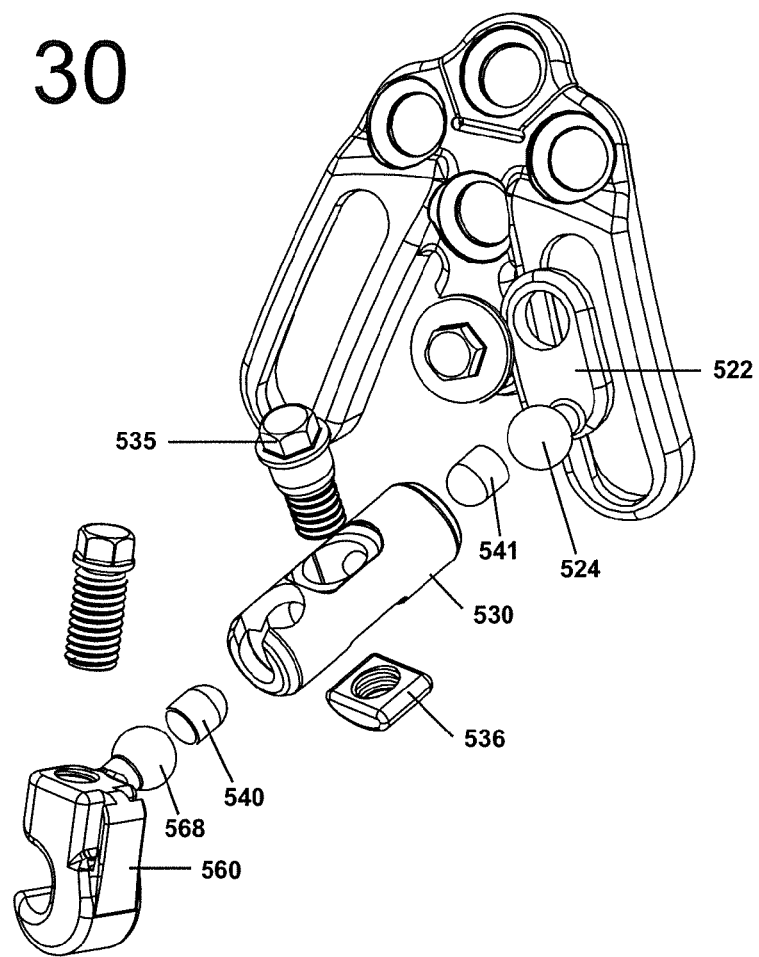
FIG. 30 is another perspective partially exploded view of the device of FIG. 27 showing the components of the slidably mounted multi-articulating arms.
Figure 31:
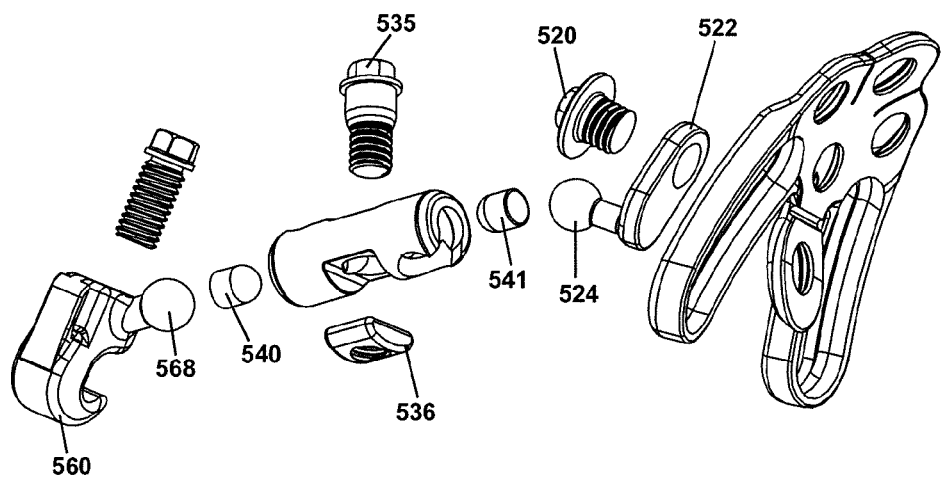
FIG. 31 is a perspective partially exploded view from the rear of the device of FIG. 27 showing the components of the slidably mounted multi-articulating arms.

One of the articulating arms 530 is shown in an exploded view in FIGS. 29, 30, and 31 in order to demonstrate locking of the arm. The arm portion 530 is a hollow sleeve-like member with narrowed collar portions at each end that provide openings with a diameter less than the diameter of the internal bore of the arm portion. A sliding member 522 that is slidably disposed in the guide track 515 of the plate member is coupled to the articulating arm 530 by a ball and socket connection 523 formed by a spherical head 524 of the sliding member 522 and a spherical cavity 528 of the arm portion 530. A side opening in the arm portion 530 allows the spherical portion 524 to be loaded into the cavity 528 of the arm 530. Similarly, the rod receiving head 560 has a spherical portion 568 that is received in a second spherical cavity 569 of the arm portion 530 to form a second ball and socket connection 567.

A locking device including a threaded locking bolt 535, friction elements 540 and 541, and a plate 536 is provided. Friction elements 540 and 541 are disposed within a bore 531 of the arm portion 530, and have tapered ends 545 and 546 that are directed toward the center of the arm. The locking bolt 535 is threaded through the plate 536 so that turning of the bolt 535 advances the bolt downward through the arm 530. Tapered abutment surfaces 537 are provided along the exterior of the bolt, and advancing the bolt 535 downward by a predetermined amount causes the abutment surfaces 537 to engage the tapered ends 545, 546 of the friction elements, forcing the friction elements 540, 541 to slide outward away from the bolt 535. The friction elements are thereby forced into contact with the spherical portion 524 of the sliding element and the spherical portion 568 of the rod receiving head 560, clamping them against their respective cavities in the arm portion 530. Thus, the movement of the locking bolt 535 transverse to the arm portion 530 is translated into axial locking forces along the axis of the arm 530 that simultaneously lock the two spherical portions 524 and 568 in place at opposite ends of the arm portion 530.

Figure 32:
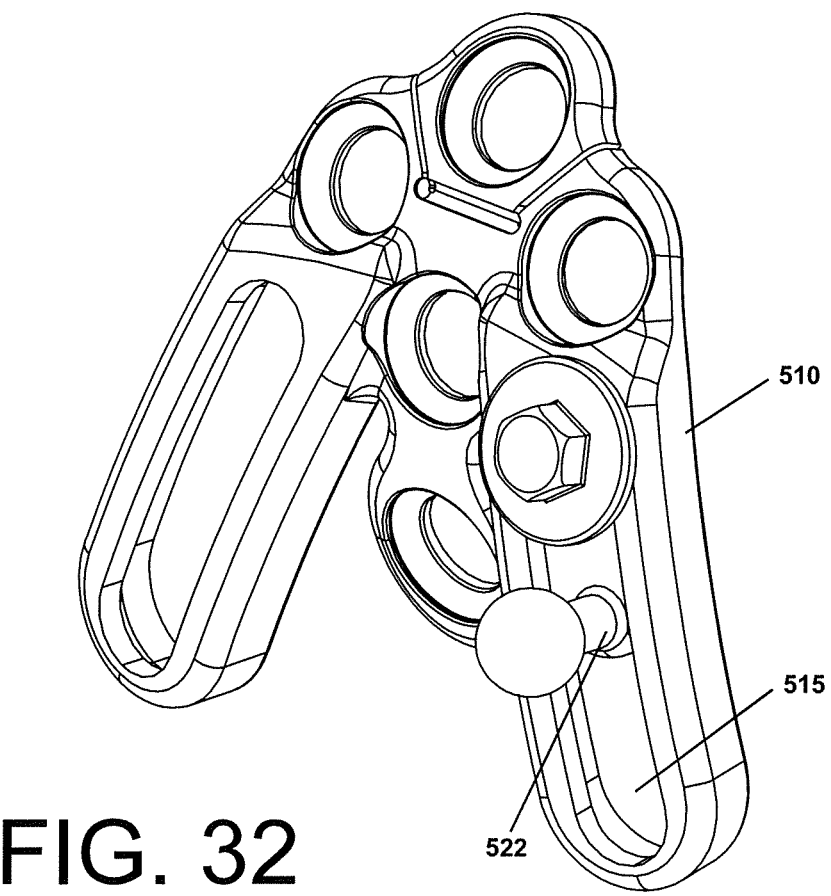
FIGS. 32 and 33 are perspective views of the plate device from FIG. 27 illustrating the sliding mechanism coupled thereto.
Figure 33:
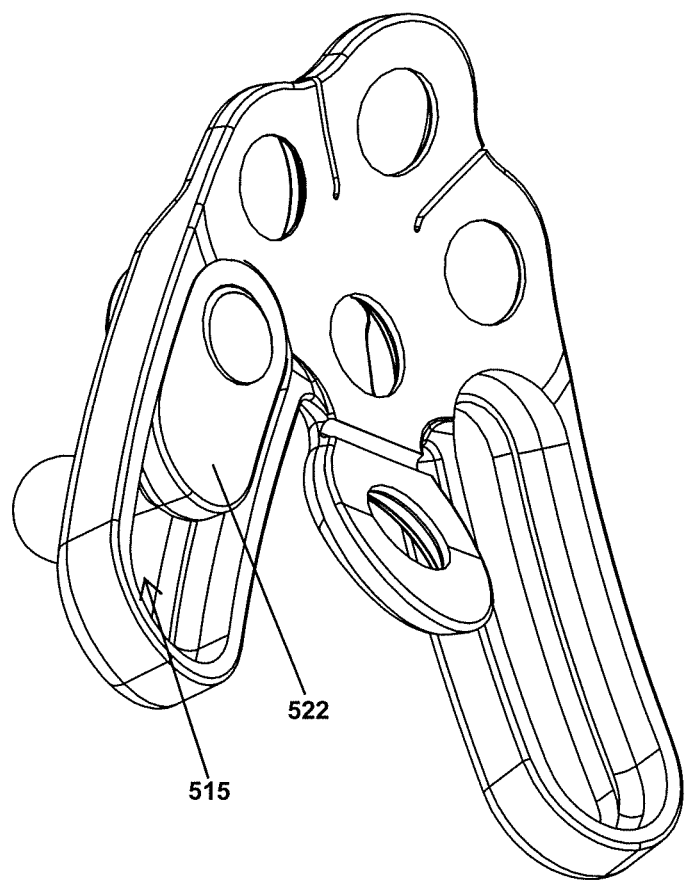

The relationship between the sliding element 522 and the guide track 515 is more clearly shown in FIGS. 32 and 33, with the articulating arm removed for an unobstructed view of the plate member 510.

Figure 34:
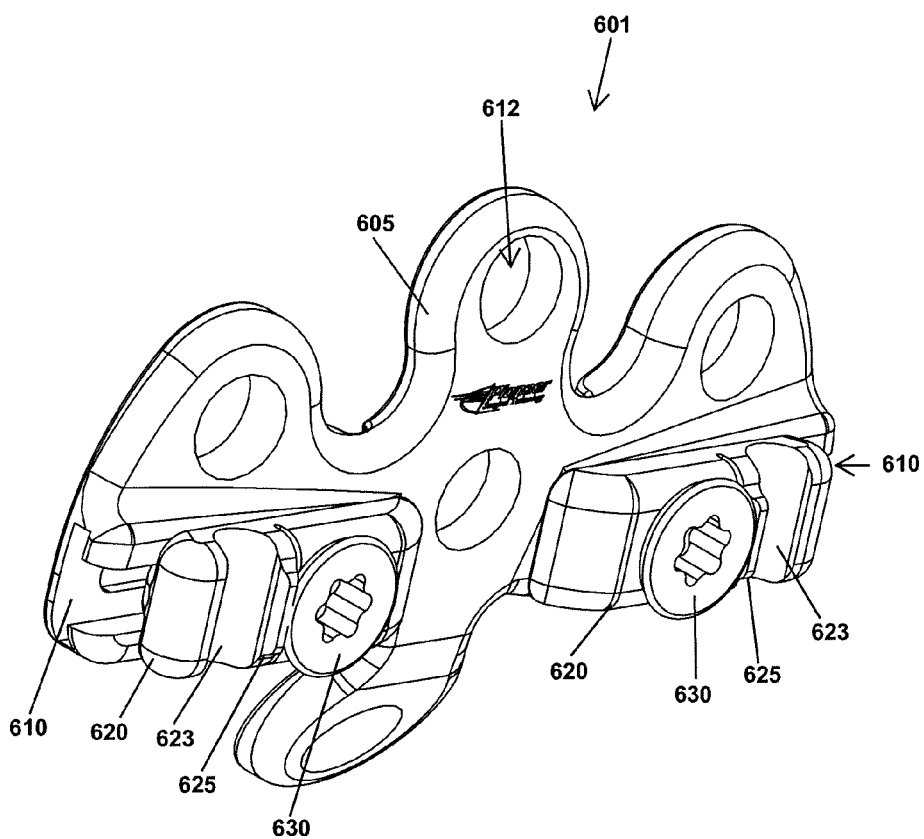
FIG. 34 is a perspective view of a plate device having sliding rod receiving members and multi-function locking actuators.
Figure 35:
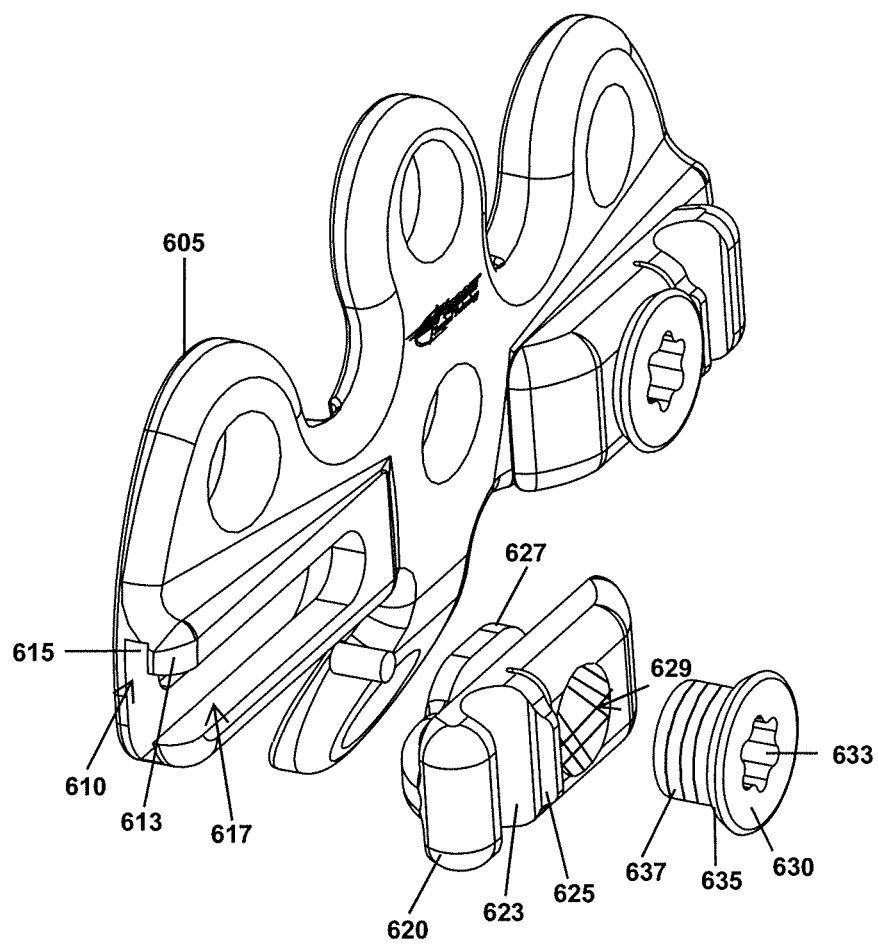
FIG. 35 is a perspective partially exploded view of the device in FIG. 35.
Figure 36:
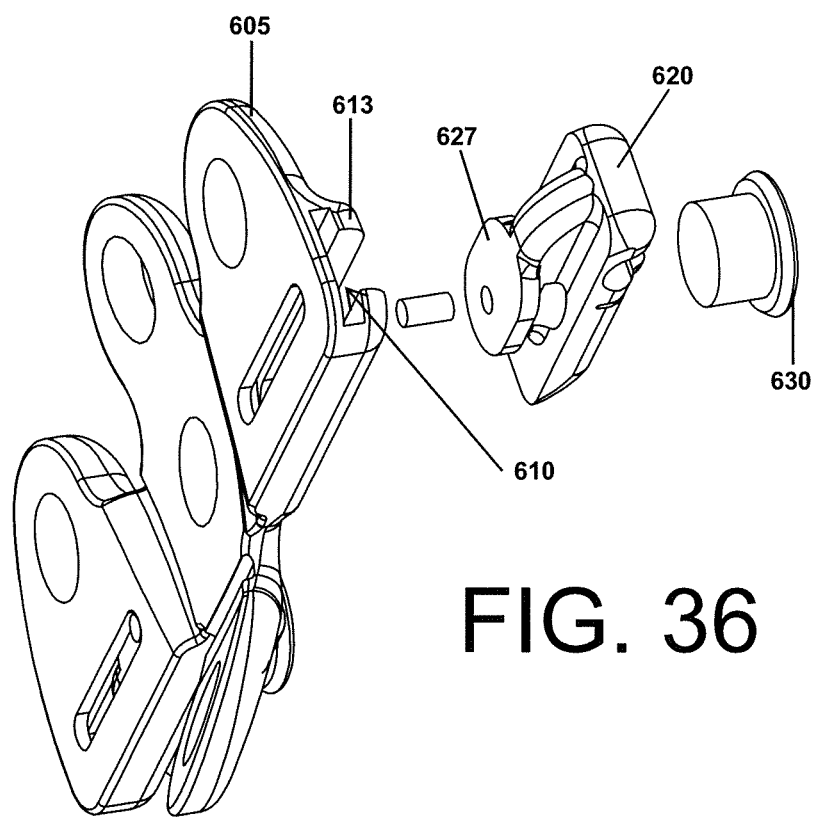
FIG. 36 is a perspective partially exploded view from the rear of the device in FIG. 35.

FIGS. 34-36 illustrate another occipital plate design with a plurality of apertures 612 for anchor devices and an easy locking feature. The plate 601 includes a pair of sliding members 623 partially disposed in guide tracks 610 for shifting laterally and medially. A single actuator 630 for each sliding member 620 locks the position of the sliding member with respect to the plate and locks the position of a spinal rod with respect to the sliding member. Each sliding member 620 includes an arcuate recess 623 for receiving a spinal rod. Adjacent the arcuate recess is a flexible portion 625 of the sliding member. Tightening of the actuator 630 shifts the flexible portion 625 away from the actuator 630, compressing the flexible portion 625 against a spinal rod positioned in the neighboring arcuate recess 623.

Simultaneously with locking the rod, the actuator 630 secures the sliding member 620 with respect to the plate member 605. As best seen in the partially exploded view of FIG. 35, the sliding member includes a clip 627 that holds the sliding member 620 along a guide track 610 in the plate. The guide track 610 includes a wider inner space 615 and a narrower window 617 that is formed by partial enclosure of the inner space 615 by a flange 613. The clip 627 of the sliding member is disposed in the wider inner space 610 of the track, and connects to the rest of the sliding member 620 through the narrow window 617. The sliding member 620 may be connected to a pin 640 or another structure that rides in a guide slot 645 to limit movement of the sliding member, preventing it from sliding out of the end of the guide track 610.

When the threaded portion 637 of the actuator 630 is advanced into a threaded throughbore 629 of the sliding member 620, the actuator abuts the plate 605, pulling the sliding portion forward so that the clip 627 abuts the flange 613 of the guide track. Friction between the clip 627 and the flange 613 inhibits sliding of the sliding member 620. As can be seen from the view in FIGS. 35 and 36, the actuator 630 is also provided with a tapered head 635 so that advancement of the actuator 630 causes camming of the tapered head 635 against the adjacent flexible portion 625 of the sliding member. The resulting shifting of the flexible portion 625 reduces the size of the arcuate recess 623, allowing the device to clamp an appropriately sized spinal rod positioned in the arcuate recess 623.

Figure 37:
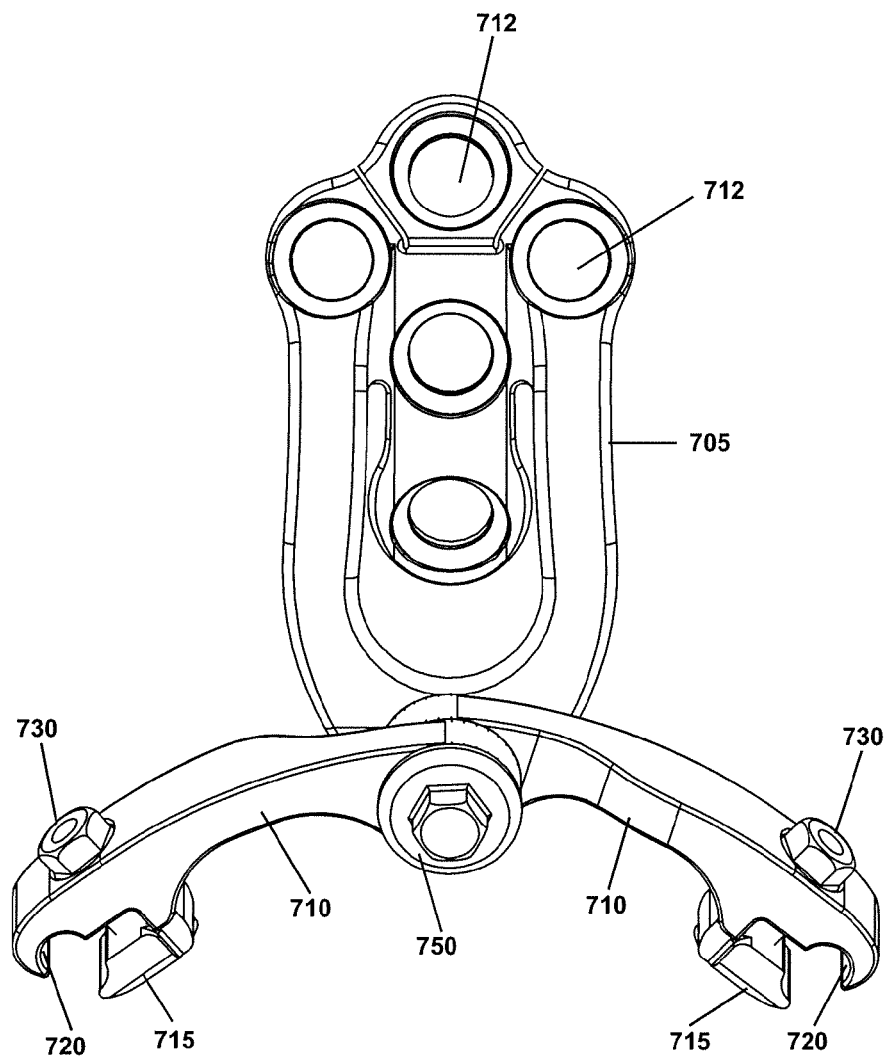
FIG. 37 is a front view of a plate device with rotatable arms.
Figure 38:
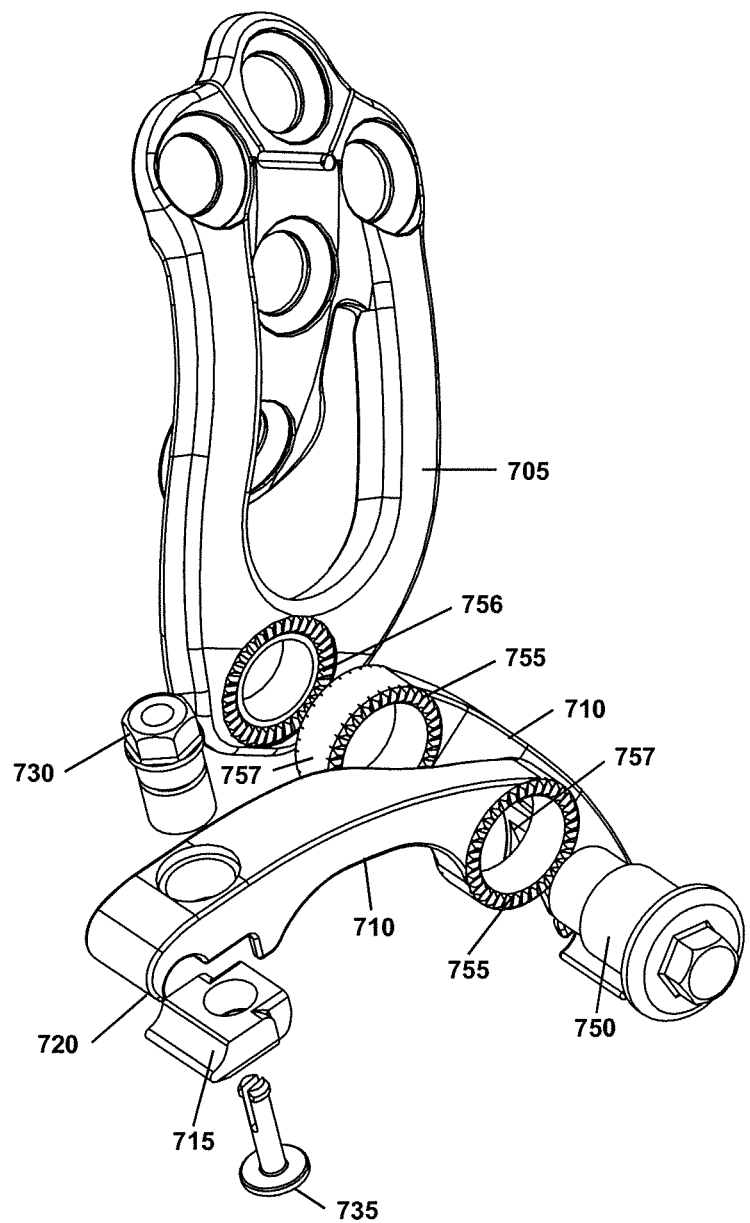
FIG. 38 is a perspective exploded view of the device from FIG. 37.
Figure 39:
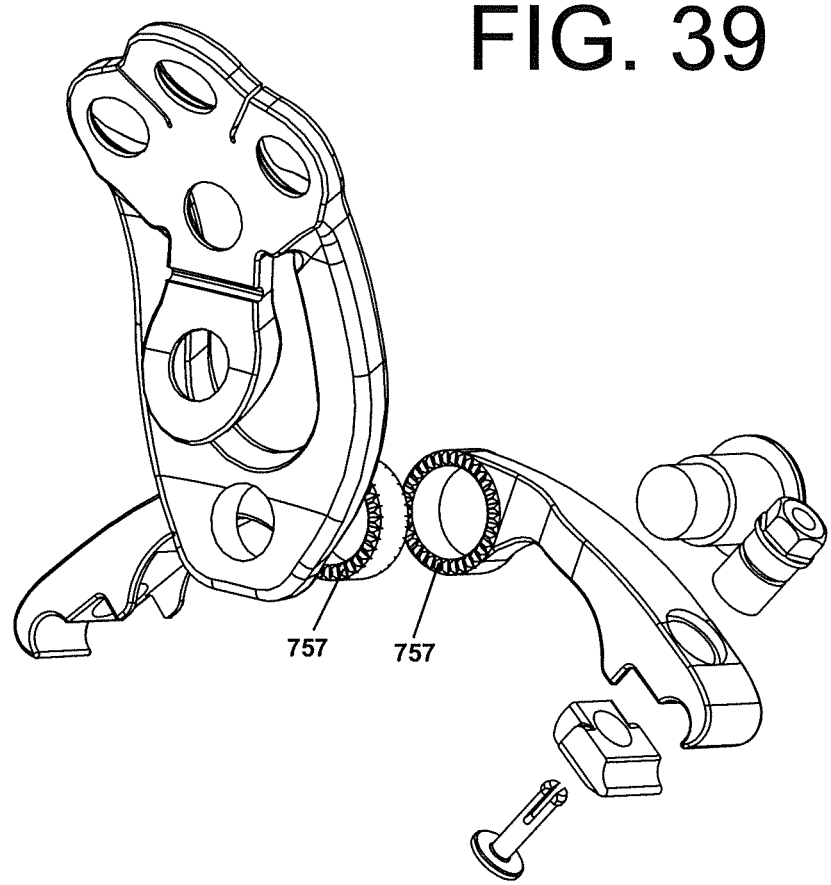
FIG. 39 is a perspective exploded view of the device from FIG. 37 from the rear.
Figure 40:
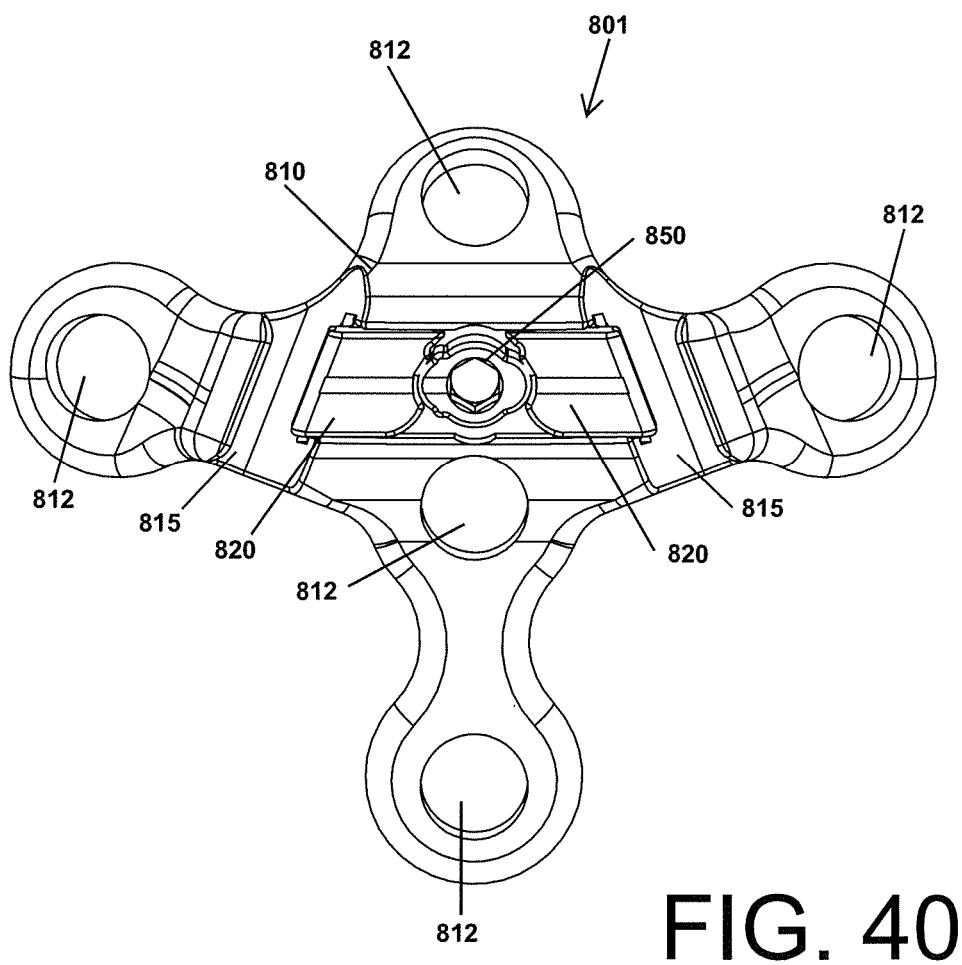
FIG. 40 is a front view of a quick-locking plate device having a single actuator to lock a pair of spinal rods.
Figure 41:
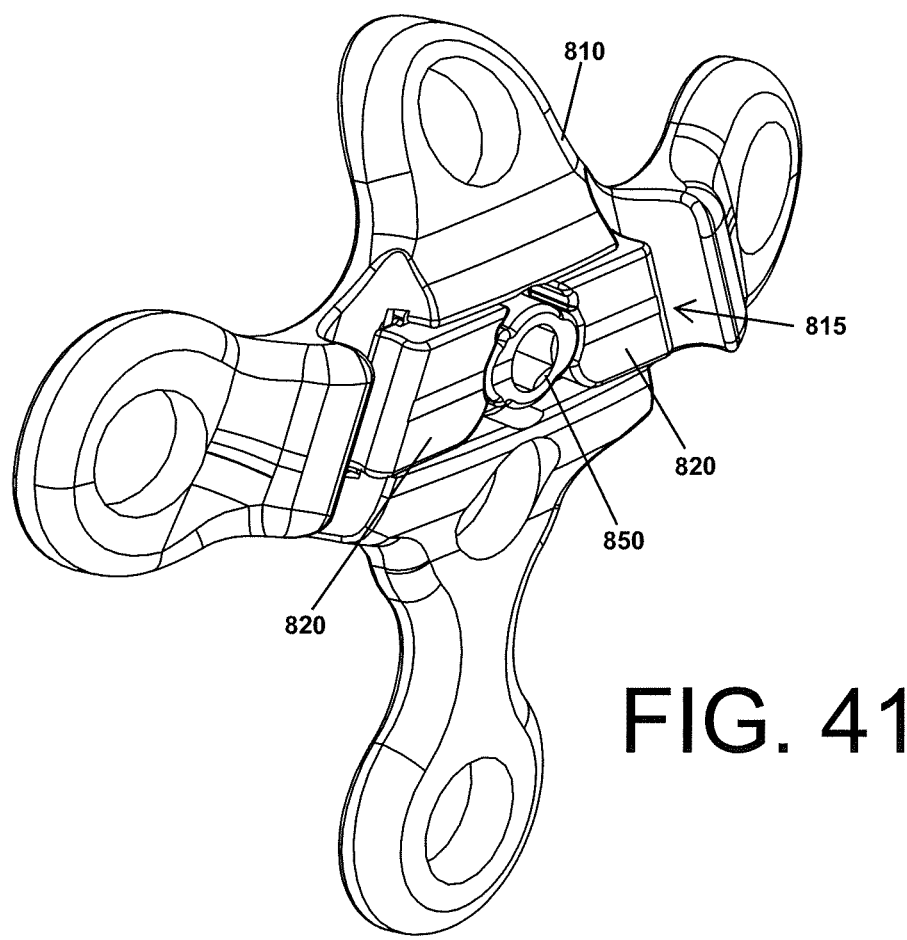
FIG. 41 is a perspective view of the device from FIG. 40.
Figure 42:
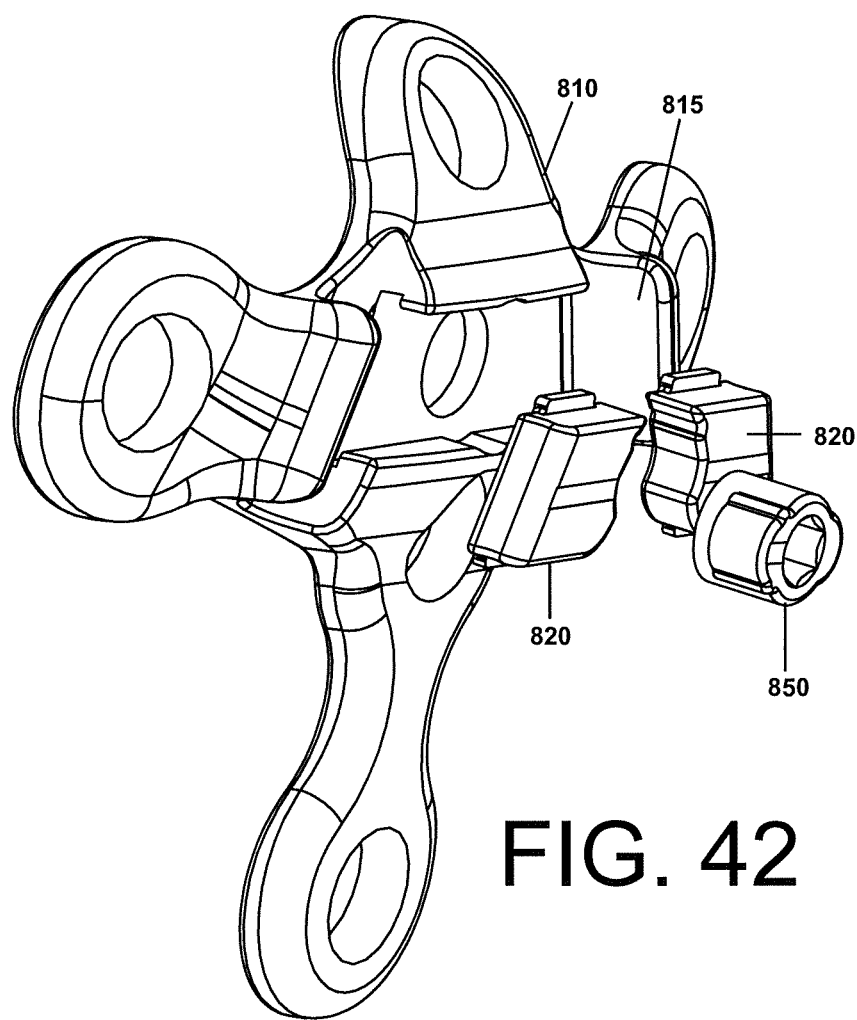
FIG. 42 is a perspective exploded view of the device from FIG. 40.
Figure 43:
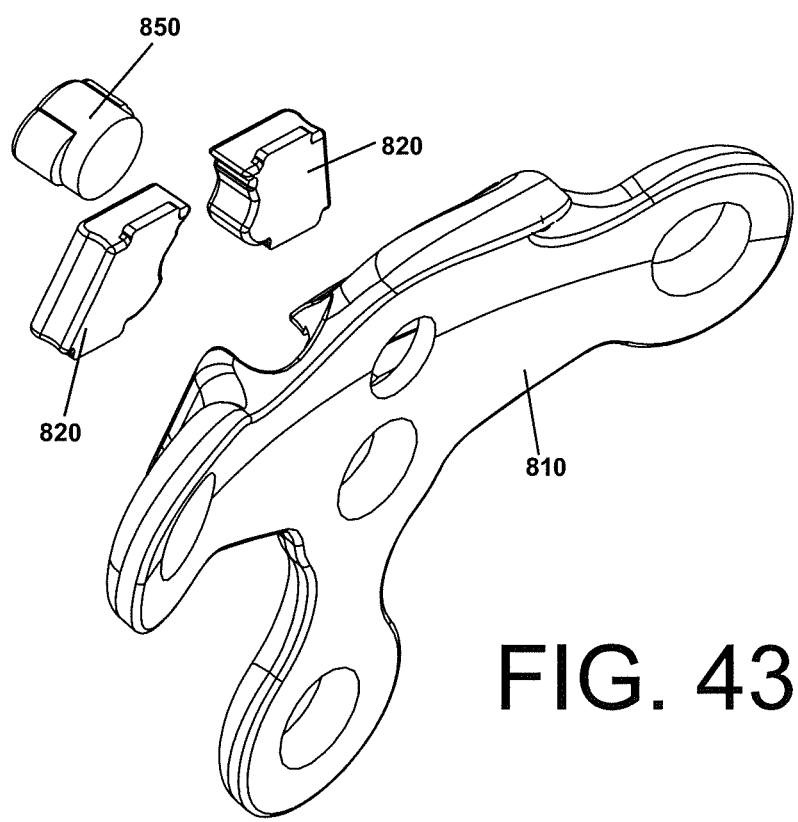
FIG. 43 is a perspective exploded view from the rear of the device from FIG. 40.

FIGS. 37-39 illustrate yet another plate device with articulating members for positioning and securing a pair of spinal rods. The device includes a plate member 705 having a plurality of openings 712 for anchor members and a pair of elongate clamp arms 710, each having a clamp jaw 715 moveably coupled to the arm. The arm further includes a rod receiving recess 720 that can be seated on a spinal rod. An actuator 730 associated with each arm draws the clamping jaw 715 upward, clamping a spinal rod between the arcuate surface 720 and the moveable jaw 715.

The arms 710 are able to pivot around a central bolt 750 that passes through both arms. Both arms are simultaneously secured against pivoting by tightening of the central bolt 750. As shown in FIGS. 38 and 39, the arms and plate are provided with arrays of teeth 755 and 757 on the front and rear sides that mesh together when the bolt 750 clamps the arms 710 against the plate member 705. The plate member also includes a circular array of teeth 756 that meshes with corresponding teeth 757 of the arms 710. In order to pivot the arms 710, the teeth 755 must be allowed to slide past one another, pushing the arms away from one another and away from the plate. This, of course, is extremely difficult when the central bolt 750 clamps the arms 710 against the plate 705. The teeth thus provide an effective inhibitor of relative motion between the arms 71 and the plate 705. if desired, washers with corresponding teeth can be positioned between the two arms and/or between the arms and the plate to adjust the distances therebetween.

A further occipital plate design with an easy locking feature is shown in FIGS. 40-43. The device 801 includes a plate body 810 including a plurality of openings for receiving anchor members. The plate body further includes a pair of recesses or grooves 815 for receiving a spinal rods. A pair of slidable locking elements 820 are provided that may slide to partially cover the recesses 815, blocking the exit of an appropriately-sized spinal rod positioned therein. The sliding members 820 are both shifted by a central asymmetrical actuator 850. Due to the asymmetrical shape of the actuator 850, rotation of the actuator forces the sliding members simultaneously outward to cover the rod recesses 815 and clamp spinal rods therein.

For instance, in the illustrated embodiment, a generally oblong rotatable actuator 850 is positioned between the two sliding members. When the longer dimension of the actuator 850 is oriented vertically, the sliding members may be positioned toward the center of the plate. However, rotating the actuator by 90 degrees to the locked position shown in FIG. 40 causes camming of the wide portions of the actuator against the sliding members 820, forcing the sliding members outward, simultaneously locking both rod recesses 815. Springs may be provided so that the sliding members 820 return to their original positions when the actuator 850 is rotated back to the unlocked position.

Figure 44:
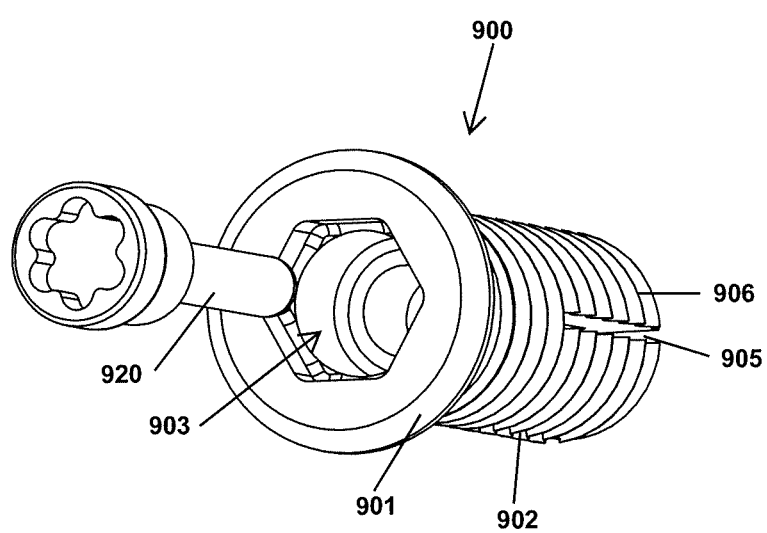
FIGS. 44 and 45 are perspective views of screws for mounting the plate members disclosed herein.
Figure 45:
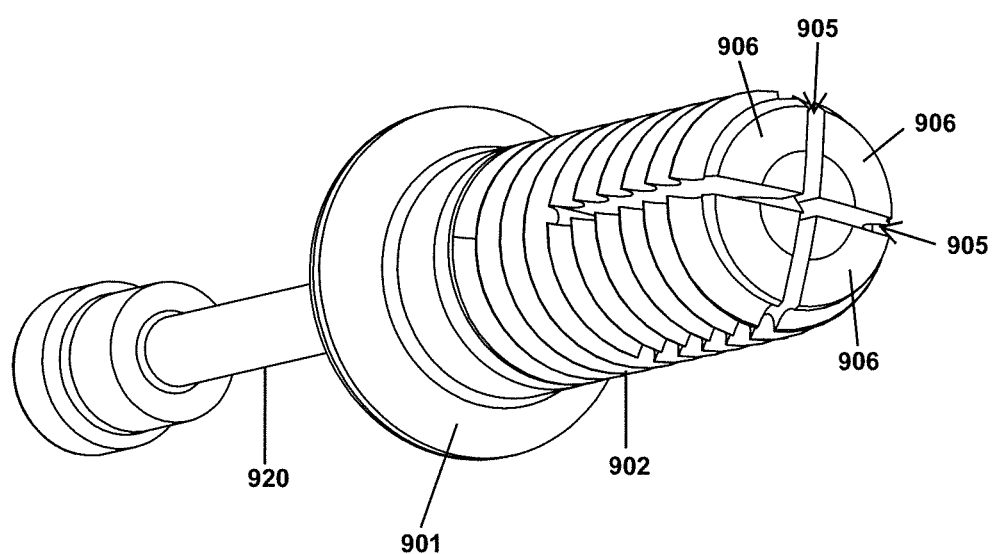

FIGS. 44 and 45 illustrate an expansion screw that may be used to mount the above-described occipital plates to the skull. The screw 900 includes a threaded body 902 and a head portion 901. The body includes one or more slits 905 to divide the body into a plurality of expandable fingers that are capable of deflecting slightly outward. The screw also includes an axial bore 903 through most of the body of the screw. After the screw is threaded into a body surface, an insertable camming element 920 may be linearly inserted through the bore 903, forcing the expandable fingers 906 of the screw body slightly outward. This expandable screw has greater holding power than traditional screws due to the increased transverse force exerted by the camming insert and the outwardly expandable finger portions. Thus, a shorter screw may be used to mount the occipital plate, requiring less penetration into the bone of the skull.

Figure 46:
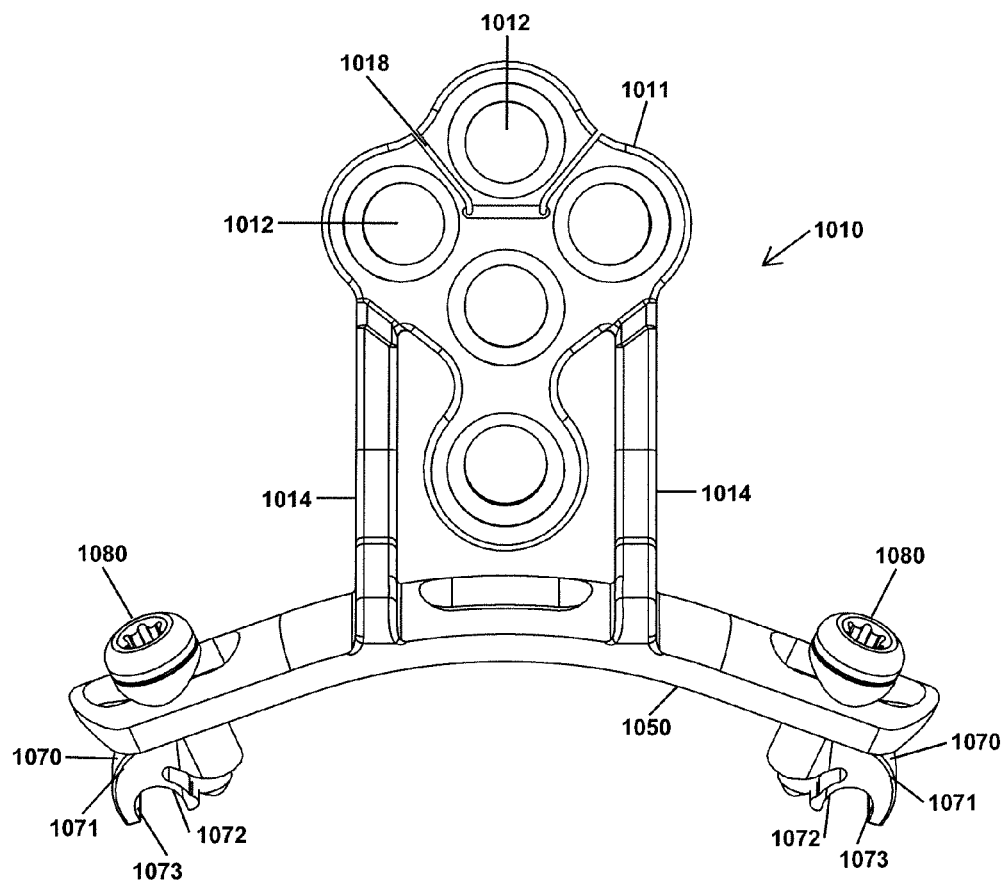
FIG. 46 is a front view of another plate device having sliding rod receiving members, flexible clamping members, and multi-function locking actuators.
Figure 47:
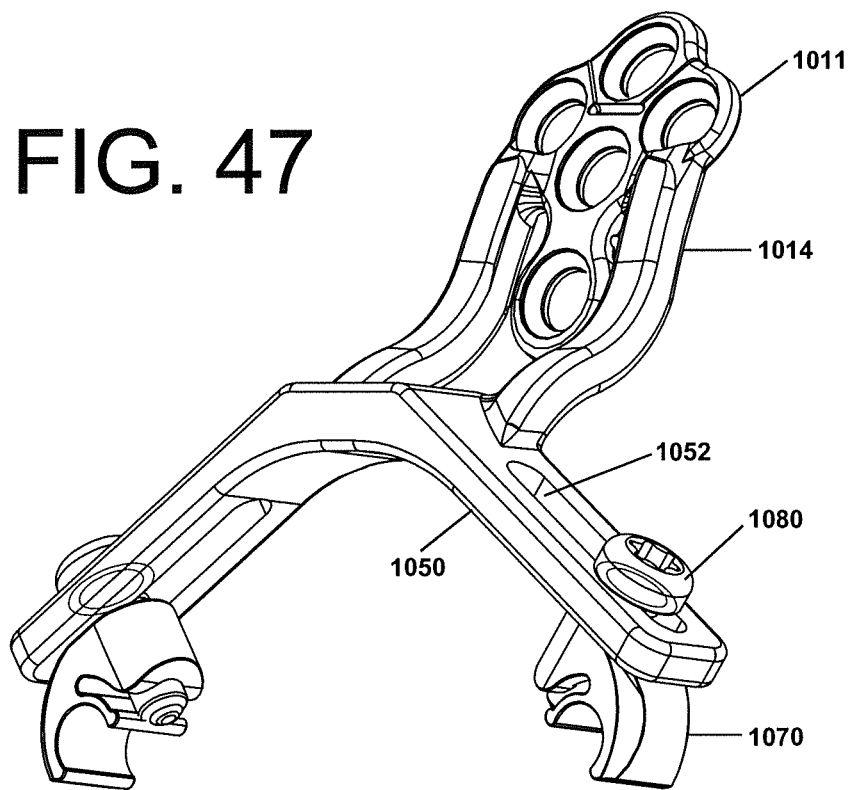
FIG. 47 is a front perspective view of the device shown in FIG. 46.
Figure 48:
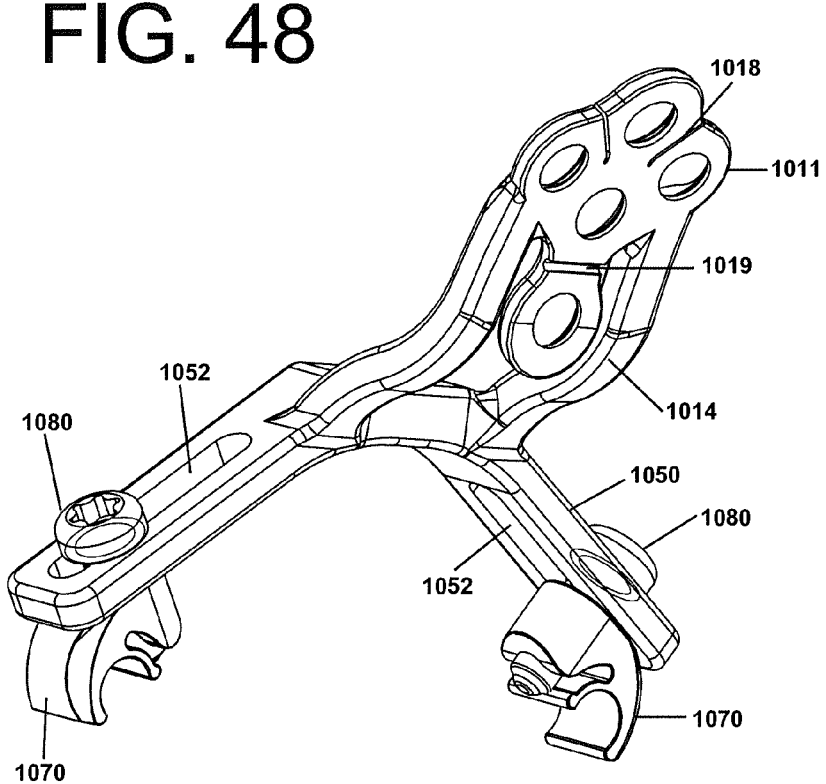
FIG. 48 is a rear perspective view of the device shown in FIG. 46.

In another aspect of the invention, a plate device as shown in FIGS. 46-49 is provided in order to stabilize spinal rods. Similarly to the device shown in FIG. 14, the device 1010 shown in FIGS. 46-49 includes a track member 1050 to which a pair of rod receiving or clamp members 1070 are slidably connected, as shown in FIGS. 14-19. In the illustrated device, a locking actuator 1080 couples each clamp member 1070 to the track member 1050, and allows relative rotation between the clamp members and the track member. The locking actuators 1080 are also disposed in guide slots 1052 formed in the track member 1050, as shown in FIG. 47, to allow sliding movement of the clamp members 1070 along a length of the track member 1050. The sliding and rotation of the clamp members 1070 along the track member 1050 allows the distance between the clamp members to be adjusted so that the clamp members 1070 may capture spinal rods having various orientations and distances from one another.

Alternatively, the clamp members may be coupled to arm portions or other portions of the plate device without requiring the device to include a track member.

As with previous devices described in this application, the illustrated plate device 1010 of FIG. 46 has a plate body 1011 that includes a number of throughholes 1012 for receiving screws or other devices for mounting the plate device to the skull of a patient. Cuts or grooves 1018 and 1019 in the plate body 1011 allows for bending of the plate to better accommodate the contours of the skull. Arms 1014 may be configured to hold the track member 1050 in a desired relationship with the plate body 1011. If desired, the arms 1014 may be hinged or articulated in order to allow the spatial relationship of the plate body 1011 and track member 1050 to be varied, and locking members may be provided to selectively prevent movement of the arms 1014 when the track member 1050 is positioned as desired.

The illustrated clamp members 1070 each include a body portion 1071 and a clamping jaw 1072 forming an arcuate recess 1073 for receiving and holding in place a spinal rod. As illustrated, the clamping jaw 1072 is a flexible portion of the clamp body that is secured against the spinal rod by the locking actuator 1080. Alternatively, the jaw portion 1072 may be a separate portion that is pivotable with respect to the clamp body 1071. The design of the illustrated clamp member 1070 and locking actuator are such that a single actuator 1080 causes each clamping member 1070 to clamp a spinal rod in place and simultaneously locks the position of that clamping member with respect to the track member 1050.

Figure 49:
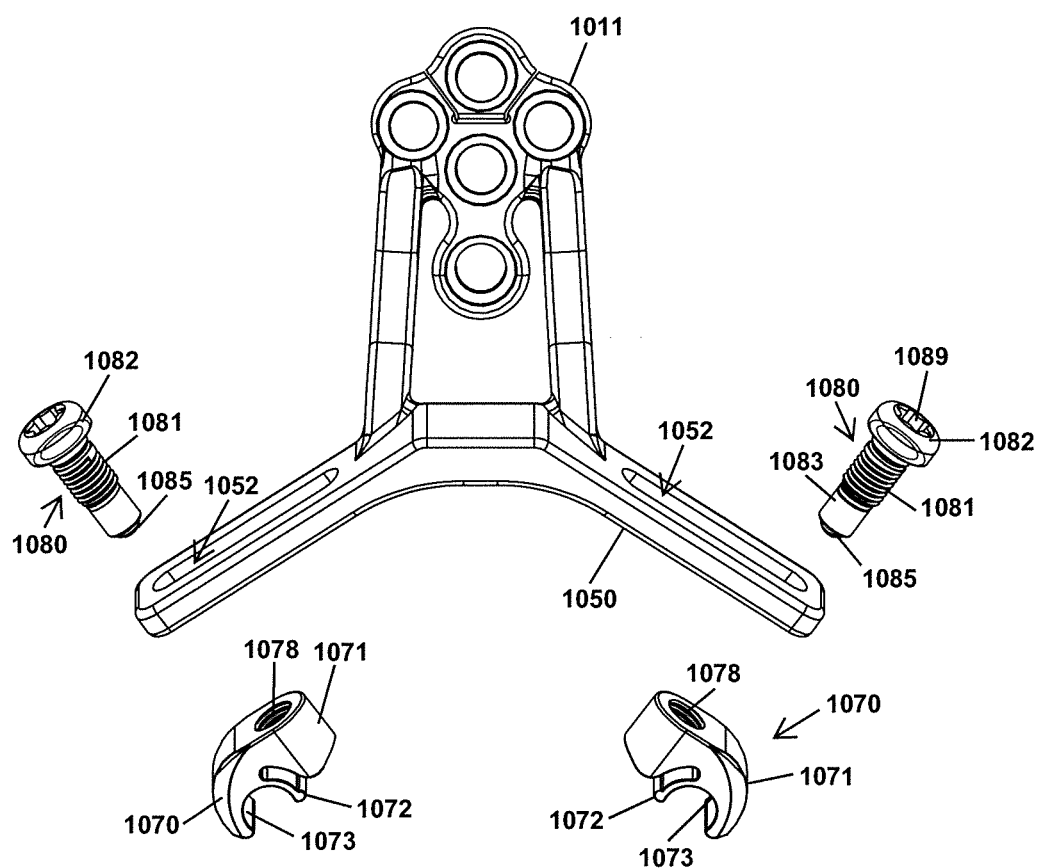
FIG. 49 is an exploded view of the device shown in FIG. 49.
Figure 50:
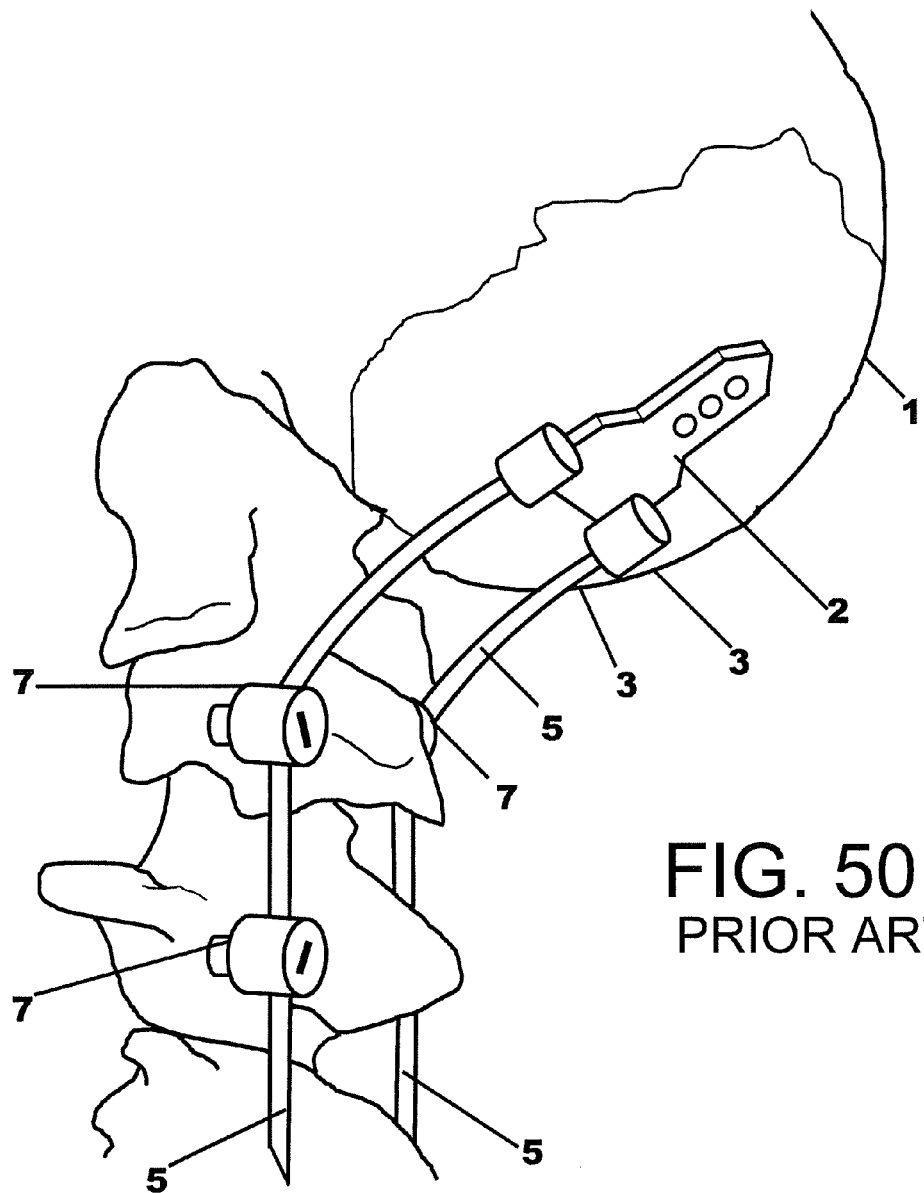
FIG. 50 is an illustration of a prior art occipital plate device for securing a pair of spinal rods.

As best shown in the exploded view of FIG. 49, each clamping member 1070 includes an arcuate recess 1073 for receiving a spinal rod. Adjacent the arcuate recess is a flexible portion 1072 of the clamping member. The locking actuator 1080 passes through a guide track opening 1052 of the track member 1050 to engage the clamp member 1070. A head portion 1082 of each locking actuator 1080 is sized and configured so that it cannot pass through the guide track openings 1052 of the track member 1050, while the shank portion 1083 of the locking actuator 1080 is configured so that it may be slidably disposed within a guide track opening 1052.

Rotation of the actuator 1080 engages threading 1081 of the actuator with a corresponding threaded bore 1078 of the clamp member 1070, coupling the clamp member 1070 to the track member 1050 and eventually clamping the track member 1050 between the head 1082 of the locking actuator 1080 and the clamp body 1071 to fix the clamp 1070 against sliding and rotation. Simultaneously, tightening of the locking actuator 1080 shifts the actuator relative to the clamp member 1070 and engages a cam surface 1085 of the actuator with the flexible clamping jaw 1072, shifting the flexible jaw portion 1072 away from the actuator 1080 and compressing the flexible portion 1072 against a spinal rod positioned in the arcuate recess 1073. In other words, rotation of the actuator 1080, for instance utilizing tool interface 1089, advances the locking actuator 1080 to simultaneously clamp the clamp body 1070 against the track member 1050 and deflect resilient jaw portion 1072 of the clamping member inward to lock a spinal rod in place.

It has been found that the unitary clamping device 1070 of FIGS. 46-49 having a clamping body and deflectable jaw portion 1072 has exceptional holding force when clamped into place with a rotatable screw-like actuator 1080 as illustrated. The locking actuator, of course, may vary from the illustrated form, and can include, for instance, non-threaded engagement features such as discontinuous flanges configured to advance the locking actuator 1080 upon rotation relative to the clamping member 1070. The clamping member may be made of various materials, but is preferably made from a flexibly resilient material such as Nitinol in order to allow for locking and unlocking of the spinal rod.

It is intended for the following claims to cover these and any other departures from the disclosed embodiment which fall within the true spirit of the invention.

What is claimed is:

1. A posterior spinal stabilization system comprising:
 a plate body including a plurality of apertures for receiving anchor members;
 a track member of the plate body including an elongate guide slot;
 at least one rod receiving member for receiving a spinal rod;
 a swivel base slideably disposed in the track member guide slot and having an arcuate head portion pivotally connected to the rod receiving member so that the rod receiving member is operable to slide along the guide slot with the arcuate head portion being spaced from the track member to allow pivoting of the rod receiving member about a plurality of different axes extending through the head portion; and
 a clamping member operable to fix the swivel base against sliding in the guide slot;
 wherein the clamping member is coupled to the track member by a locking actuator operable to shift the clamping member between an unlocked configuration, wherein the swivel base is slideable along the guide slot, and a locked configuration, wherein the swivel base is fixed against sliding in the guide slot.

2. The posterior spinal stabilization system of claim 1, wherein the plate body includes a bone engaging portion having the plurality of apertures and the guide slot is oriented in a plane transverse to the bone engaging portion of the plate body.

3. The posterior spinal stabilization system of claim 1, wherein the arcuate head portion of the swivel base has a spherical configuration.

4. The posterior spinal stabilization system of claim 1, wherein the arcuate head portion includes a compression gap for providing a snap-lock connection between the head portion and the rod receiving member.

5. The posterior spinal stabilization system of claim 1, wherein the guide slot includes an access end opening to allow the swivel base to be slid into the guide slot; and a shiftable stop member associated with the track member operable to block the end opening of the guide slot to keep the swivel base from exiting the guide slot.

6. The posterior spinal stabilization system of claim 1, further comprising a locking member operable to simultaneously fix the spinal rod to the rod receiving member and fix the rod receiving member relative to the arcuate head portion of the swivel base.

7. The posterior spinal stabilization system of claim 1, wherein the track member includes an upper side and a lower side, and the arcuate head portion of the swivel base is spaced from the upper side of the track member.

8. The posterior spinal stabilization system of claim 1, wherein the track member comprises a second elongate guide slot; and
a second rod receiving member for receiving an additional spinal rod;
a second swivel base slideably disposed in the second track member guide slot and having an arcuate head portion pivotally connected to the second rod receiving member so that the second rod receiving member is operable to slide along the second guide slot with the arcuate head portion being spaced from the track member to allow pivoting of the second rod receiving member about a plurality of different axes;
wherein the clamping member is operable to fix each swivel base against sliding in the respective guide slots.

9. A posterior spinal stabilization system comprising:
a plate body including a plurality of apertures for receiving anchor members;
a track member of the plate body including an elongate guide slot;
at least one rod receiving member for receiving a spinal rod; and
a swivel base slideably disposed in the track member guide slot and having an arcuate head portion pivotally connected to the rod receiving member so that the rod receiving member is operable to slide along the guide slot with the arcuate head portion being spaced from the track member to allow pivoting of the rod receiving member about a plurality of different axes extending through the head portion;
wherein the track member is connected to the plate body by an arm member configured to space the track member from a patient's skull and toward the patient's spine when the plate body is mounted to an occipital region of the skull.

10. The posterior spinal stabilization system of claim 9, wherein the arm member has a curved configuration to space the track member from the patient's skull and toward the patient's spine when the plate body is mounted to an occipital region of the skull.

11. A posterior spinal stabilization system, comprising:
a plate body including a plurality of apertures for receiving anchor members;
a track member of the plate body including an elongate guide slot;
a yoke member for receiving a spinal rod; and
a slideable connection between the yoke member and the track member configured to allow the yoke member to slide in the guide slot and to shift polyaxially with respect to the track member for receiving the spinal rod in the yoke member in a selected one of a plurality of different orientations with respect to the track member;
wherein the track member is connected to the plate body by an arm member that is configured to position the track member spaced from a patient's skull and toward the patient's spine when the plate body is mounted to an occipital region of the skull.

12. The posterior spinal stabilization system of claim 11, further comprising a clamping member operable to fix the yoke member relative to the guide slot, wherein the yoke member is operable to shift polyaxially with respect to the track member when the yoke member is fixed with respect to the guide slot by the clamping member.

13. The posterior spinal stabilization system of claim 11, wherein the arm member has a curved configuration to space the track member from the patient's skull and toward the patient's spine when the plate member is mounted to an occipital region of the skull.

14. The posterior spinal stabilization system of claim 11, wherein the slideable connection includes a swivel base slideably disposed in the guide slot and connected to the yoke member to allow the yoke member to shift along the guide slot, the swivel base including a spherical head portion configured to matingly engage with the yoke member to allow the yoke member to pivot polyaxially with respect to the spherical head portion.

15. The posterior spinal stabilization system of claim 14, further comprising a locking member operable to simultaneously fix the spinal rod to the yoke member and fix the yoke member relative to the swivel base.

16. The posterior spinal stabilization system of claim 11, wherein the guide slot includes an access end opening to allow the yoke member to be slideably connected to the guide slot; and
a shiftable stop member associated with the track member operable to block the end opening of the guide slot to keep the yoke member from exiting the guide slot.

17. A posterior spinal stabilization system, comprising:
a plate body including a plurality of apertures for receiving anchor members;
a track member of the plate body including an elongate guide slot;
a yoke member for receiving a spinal rod;
a slideable connection between the yoke member and the track member configured to allow the yoke member to slide in the guide slot and to shift polyaxially with respect to the track member for receiving the spinal rod in the yoke member in a selected one of a plurality of different orientations with respect to the track member;
a clamping member operable to fix the yoke member relative to the guide slot, wherein the yoke member is operable to shift polyaxially with respect to the track member when the yoke member is fixed with respect to the guide slot by the clamping member; and
a locking actuator operable to shift the clamping member between an unlocked configuration, wherein the yoke member is shiftable along the guide slot, and a locked configuration, wherein the yoke member is fixed with respect to the guide slot.

18. A posterior spinal stabilization system, comprising:
a plate body including a plurality of apertures for receiving anchor members;
a track member of the plate body including an elongate guide slot;
a yoke member for receiving a spinal rod;
a slideable connection between the yoke member and the track member configured to allow the yoke member to slide in the guide slot and to shift polyaxially with respect to the track member for receiving the spinal rod in the yoke member in a selected one of a plurality of different orientations with respect to the track member;

wherein the slideable connection includes a swivel base slideably disposed in the guide slot and connected to the yoke member to allow the yoke member to shift along the guide slot, the swivel base including a spherical head portion configured to matingly engage with the yoke member to allow the yoke member to pivot polyaxially with respect to the spherical head portion; and an insert member engaged with the spherical head portion within the yoke member for forming a ball and socket connection with the spherical head portion, the insert member being configured to engage the spinal rod.

* * * * *